US006696289B1

(12) United States Patent
Bae et al.

(10) Patent No.: US 6,696,289 B1
(45) Date of Patent: Feb. 24, 2004

(54) REPLICATION-COMPETENT RECOMBINANT SABIN TYPE 1 STRAIN OF POLIOVIRUS

(75) Inventors: Yong Soo Bae, Taejon (KR); Hye Rhan Jung, Taejon (KR)

(73) Assignee: Creagene Inc., Taejon (KR)

( * ) Notice: Subject to any disclaimer, the term of this patent is extended or adjusted under 35 U.S.C. 154(b) by 0 days.

(21) Appl. No.: 09/284,349

(22) PCT Filed: Aug. 7, 1998

(86) PCT No.: PCT/KR98/00242

§ 371 (c)(1),
(2), (4) Date: Jun. 4, 1999

(87) PCT Pub. No.: WO99/07859

PCT Pub. Date: Feb. 18, 1999

(30) Foreign Application Priority Data

Aug. 7, 1997 (KR) ............................................. 97-37812

(51) Int. Cl.[7] ............................................. C12N 15/74
(52) U.S. Cl. ............................. 435/320.1; 424/188.1; 424/208.1; 435/235.1; 435/236
(58) Field of Search ........................... 424/188.1, 208.1; 435/320.1

(56) References Cited

U.S. PATENT DOCUMENTS

| | | | | |
|---|---|---|---|---|
| 5,571,712 A | * | 11/1996 | Haynes et al. ............ | 435/240.2 |
| 5,580,773 A | * | 12/1996 | Kang et al. ................. | 435/236 |
| 5,965,124 A | * | 10/1999 | Feinberg et al. .......... | 424/93.21 |

OTHER PUBLICATIONS

Andino, R., et al., "Engineering poliovirus as a vaccine vector for the expression of diverse antigens.", Science, (Sep. 2, 1994) 265:1448–1451.*

Yim, Tang, & Andino, Poliovirus Recombinants Expressing Hepatitis B Virus Antigens Elicited a Humoral Immune Response in Susceptible Mice, Virology 218, pp 61–70 (1996).

Tang, Rij, Silvera, & Andino, Toward a Poliovirus–Based Simian Immunodeficiency Virus Vaccine: Correlation between Genetic Stability and Immunogenicity, Journal of Virology, vol. 71, No. 10, Oct. 1997, p. 7841–7850.

Mueller & Wimmer, Expression of Foreign Proteins by Poliovirus Polyprotein Fusion: Analysis of Genetic Stability Reveals Rapid Deletions and Formation oif Cardioviruslike Open Reading Frames, Journal of Virology, vol. 72, No. 1, Jan. 1998, p. 20–31.

Girard, Couderc, Destombes, Thiesson, Delpeyroux & Blondel, Poliovirus Induces Apoptosis in the Mouse Central Nervous System, Journal of Virology, vol. 73, No. 7, Jul. 1999, p. 6066–6072.

Crotty, Lohman, Lu, Tang, Miller & Andino, Mucosal Immunization of Cynomolgus Macaques with Two Serotypes of Live Poliovirus Vectors Expressing Simian Immunodeficiency Virus Antigens: Stimulation of Humoral, Mucosal, and Cellular Immunity, Journal of Virology, vol. 73, No. 11, Nov. 1999, p. 9485–9495.

Freistadt & Eberle, Correlation between Poliovirus Type 1 Mahoney Replication in Blood Cells and Neurovirulence, Journal of Virology, vol. 70, No. 9, Sep. 1996, p. 6486–6492.

Mandl, Hix & Andino, Preexisting Immunity to Poliovirus Does Not Impair the Efficacy of Recombinant Poliovirus Vaccine Vectors, Journal of Virology, vol. 75, No. 2, Jan. 2001, p. 622–627.

* cited by examiner

*Primary Examiner*—Laurie Scheiner
*Assistant Examiner*—Jeffrey S. Parkin
(74) *Attorney, Agent, or Firm*—Mathews, Collins, Shepherd & McKay, P.A.

(57) ABSTRACT

A replication-competent recombinant Sabin type 1 poliovirus vector containing a sequence coding for multiple cloning site and 3C-protease cleavage site is provided. This vector makes it easy to introduce various vaccine genes from infectious viruses to the Sabin 1 poliovirus, and facilitates to produce chimeric Sabin 1 polioviruses that are expected to be powerful oral mucosal vaccines against several infectious viral diseases.

13 Claims, 17 Drawing Sheets

```
           735                                              771
    5'-GTATCATA ATG GGT GCT CAG GTT TCA TCA CAG AAA GT---3'
                M   G   A   Q   V   S   S   Q   K

SstII    HpaI     EagI                       3C
            CCG CGG GTT AAC CGG CCG GCT TTG TTC CAA       ↓
             P   R   V   N   R   P   A   L   F   Q pTZ-PVS-3m
```

```
          2468              3C                   2497
            ←——— VP3 ————  ↓  ———— VP1 ————→
    5'-GCG CTA GCA CAG/GGA TTA GGT CAG ATG CTT-3'
        A   L   A   Q   G   L   G   Q   M   L

ApaI    HpaI     XhoI
        /GGG CCC GTT AAC CTC GAG AAG GCA CTT GCG CAA/
          G   P   V   N   L   Q   K   A   L   A   Q
         ↑                                          ↑
         3C                                         3C pTZ-PVS-4m
```

Plasmid map: pTZ-PVS-3m with pTZ-18/R (2.9kbp), pTZ-PVS(1) (10.4kbp), SABIN 1 cDNA (7.5kbp). Sites: PT7, EcoRI (1), EcoRI, SalI (7440), BanII (905), PstI (1813), PstI (2243), (2480), (3417), PstI (3520), BanII, position 745.

REPLICATION-COMPETENT RECOMBINANT SABIN TYPE 1 STRAIN OF POLIOVIRUS

BACKGROUND OF THE INVENTION

1. Field of the Invention

The present invention relates to a vector system useful for developing live viral vaccines. More particularly, it relates to replication-competent recombinant Sabin type 1 strain of poliovirus, which can be used for the development of live viral vaccine capable of inducing mucosal immunity.

2. Description of the Prior Arts

Recently it has been reported that various infectious viral disease, which were well known to be spread by blood-mediated routes such as blood transfusions, homosexual intercourse, or sharing of, syringes, also may be transmitted by heterosexual intercourse. In the case of AIDS (Acquired Immunodeficiency Syndrome), the number of heterosexual transmission is far greater than that of the blood-mediated cases (Stingl et al., J. Am. Aca. Dermatol., 22, 1210, 1988). In Korea, 363 out of 527 HIV-1 positive patients are heterosexuals while 99 are infected via homosexual routes (National Institute of Health, Korea, Communicable Diseases Monthly Report, April of 1996). These reports strongly suggest that the HIV-1 can be transmitted through mucosal tissues around the genital organs without blood mediation.

Several papers have reported that HIV-1 transmission and spreading are likely to be initiated by the infection of Langerhans cells or dendritic cells (DCs) at the mucosal tissues. Infected cells return to lymph node to deliver antigen, well known as homing property, where the viral replication occurs, resulting in viremia and AIDS progression. In other words, those who have heterosexual intercourse with HIV-1 infected patients will have Langerhans cells or DCs infected with HIV-1 in mucosal area of the urogenital organs, and the infected DCs return to lymph nodes, activate $CD4^+$ T-cells in lymph nodes and propagate HIV, resulting in depletion of $CD4^+$ T-cells followed by AIDS progression (Tschachler et al., J. Inves., Dermator, 88, 238, 1987; Langhoff et al., Proc. Natl.Acad.Aci. USA, 88, 7998, 1991; Patterson & Knight, J. Gen. Virol., 68, 1177, 1987; Patterson et al., Immnol., 72, 361, 1991; Cameron et al., Science, 257, 383, 1992; Embreston et al., Nature, 362, 369, 1993; Fauci, Science, 262, 1011, 1993; Pantleo et al., Nature, 362, 355, 1993; Adema et al., Nature, 387, 713, 1997). These experimental results were substantiated by in vivo experiments by addressing that the Macaque monkeys treated with SIV (Simian immunodeficiency Virus) on their genital organs became infected and then showed AIDS symptom (Miller & Gardner, J. AIDS, 4, 1169, 1991; Miller et al., 3. Virol, 63, 4277, 1989). Moreover, since most of the infectious viral diseases are spread by first infection of mucosal tissues at respiratory, digestive or urogenital organs, mucosal vaccine development is highly recommended to prevent infectious viral. In particular, the common mucosal immune system—immunization at one locus can induce identical immunity to the other mucosal areas in the living body, special characteristics of mucosal immunity, encourages many researchers to develop mucosal vaccine (Kott, Science, 266, 1335, 1994; Cease & Verzofsky, Ann. Rev. Immunol., 12, 923, 1994).

Since long ago, smallpox virus has been proposed as a live viral vaccine vehicle. Recombinant vaccinia virus produced by introducing a vaccine gene into smallpox viral genome was reported to induce cytotoxic T lymphocyte in the immunized monkey. But has not yet been allowed to apply it to human because it may cause a vaccinia syndrome to the immunized individuals when overpropagated. To avoid the possibility, an attenuated vaccinia virus was suggested as a vaccine vehicle instead of virulent strain, but it failed to induce an effective immuniity (Cooney et al., Lancet, 337, 567, 1991; Tartaglia et al., Virol., 188, 217, 1992).

Adenovirus having a smaller genome (34 kbp) than that of vaccinia virus was also proposed as a vaccine vector (Natuk et al., Proc. Natl. Acad. Sci. USA, 89, 7777, 1992; Gallichar et al., J. Infec. Dis., 168, 622, 1993). But the recombinant adenoviruses still have a limitation of side effects, such as conjuctivitis or corneitis, which should be solved for adenovirus to be used as a mucosal vaccine vector.

Poliovirus contains a positive sense single-stranded RNA of 7.4 Kb nucleotides, which encodes an unique open-reading frame of a long polyprotein (Kitamura et al., Nature 291, 547, 1981). Recently, several groups are trying to develop a poliovirus as a vaccine vehicle for its well-known and attractive advantages—safe, easy to administration, economy, and above all having capacity to induce effective life-long mucosal immunity, which is strongly recommended for an ideal vaccine.

Followings are summary of the published vaccine researches in association with poliovirus developed as a vaccine vehicle:

(1) It was proposed to substitute some portion of VP1, major outer capsid protein of poliovirus with presumed vaccine epitopes of HIV such as gp41, PND (Principle Neutralizing Domain) or gp120. The chimeric virus produced from the genetic recombination effectively induced antibody depending on the characteristics of the epitopes (Burke et al., Nature, 332, 81, 1988; Burke et al., J.Gen. .Virol. 70,2475, 1989; Evans et al., Nature, 385, 1989; Dedieu et al., J. Virol., 66, 3161, 1992; Rose et al., J. Gen. Virol., 75, 969, 1994). However, this chimeric virus has a size limitation for the Morrow and his introduced vaccine gene. Chimeric poliovirus could not be assembled properly in the infected cells when the inserted vaccine epitope is larger than 25 amino acid residues.

(2) Morrow and his colleagues (Porter et al., J. Virol., 69, 1548, 1993; Ansaradi et al., Cancer Res., 54, 6359, 1994, Porter et al., J. Virol. 70, 2643, 1996, Porter et al., Vaccine 15, 257, 1997) have suggested poliovirus minireplicon, in which poliovirus structural genes are replaced by foreign sequences, to develop poliovirus-mediated mucosal vaccines. In case of poliovirus minireplicon, the replication defective recombinant viral genome must be co-transfected with other capsid protein-expressing vector for packaging of chimeric viral genome (Porter et al., J. Virol., 69, 1548, 1995). Moreover, high titer of minireplicon is required for vaccination to induce effective mucosal immunity because it works as replication-defective target-specific immunogen rather than live viral vaccine.

(3) Recently, a new strategy was suggested for expression of foreign antigens in the replication-competent recombinant polioviruses by Mattion et al (J. Virol. 68, 3925, 1994) and Andino et al (Science, 265, 1448, 1994). They have introduced a new polylinker region and 3C protease-recognition site on the N-terminal end of the polyprotein of poliovirus. According to this system, foreign gene, cloned in-frame with the poliovirus open reading frame, is followed by an artificial 3C protease site, to allow proteolytic cleavage of the foreign protein from the poliovirus polyprotein. The exogenous nucleic acid is incorporated directly into the poliovirus genome. The exogenous sequences are expressed during virus replication as part of the virus polyprotein and subsequently processed by virus-encoded proteases to produce free antigen and mature viral protein. The foreign antigen is not packaged in the virion but released into the cytoplasm. The prinicle of this method is based on the characteristics of poliovirus-specific 3C-protease published previously. 3C-protease recognizes specific amino acid sequence and then cleaves it at the junction between Glu(Q)/Gly(G) (Hanecak et al., Proc. Natl. Acad. Sci. USA 79, 3793, 1982), and the proteolysis occurs within the intramolecule of long polyprotein (Palmenberg and Reuckert, J. Virol., 41, 244, 1982; Hanecak et al, Cell 37, 1063, 1984). These phenomena are generally observed in picornavirus family (Palmenberg et al., J. Virol. 32, 770, 1979; Palmenberg and Reuckert, J. Virol., 41, 244, 1982). The alanine(A) residue in the P4 position of the Q/G cleavage site (AXXQG; SEQ ID NO: 21) has been confirmed several times to be essential for effective recognition and cleavage by 3C-protease (Nicklinson et al., Biotechnology 4, 33, 1986; Pallai et al., J. Bio. Chem., 264, 9738, 1989; Cordingley et al., J. Virol., 63, 5037, 1989; Orr et al., J. Gen. Virol., 70, 2931, 1989; Petithory et al., Proc. Natl. Aca. Sci. USA 88, 11510, 1991; Blair and Semler, J. Virol. 65, 6111, 1991). Based on these experimental results, Mattion and his colleagues introduced (J. Virol. 68, 3925, 1994) multiple cloning site and 3C-protease cleavage site into N-terminal of Sabin type 3 strain of poliovirus and constructed chimeric poliovirus expressing rotavirus VP7. Andino and his colleagues (Science, 265, 1448, 1994) constructed recombinant Mahoney vector (MoV-1.4) by introducing multiple cloning site and 3C-protease cleavage site into the N-terminal end of the long polyprotein of poliovirus Mahoney strain. They produced chimeric poliovirus by cloning various HIV-1 subgenomes into the vector (Science, 265, 1448, 1994). Andino group has reported that the chimeric poliovirus expressing HIV-1 nef gene induced effective mucosal immunity in monkey two weeks after immunization through rectum (Andino et al., Science, 265, 1448, 1994). Nevertheless, the recombinant Mahoney poliovirus is not applicable to human without further detoxification steps since Mahoney strain of poliovirus is a deadly virulent neurotropic virus, which infects central nervous system of primates through the primary infection of digestive organ, resulting in causing paralytic poliomyelitis. Whereas, Meuller and Wimmer (J. Virol., 72, 20–31, 1998) reported that the recombinant virus obtained by cloning green fluorescence protein gene (gfp:252aa) and HIV-1 gag gene into Andino's Mahoney vector were not so much genetically stable during the passages as reported previously by Andino et al. (Science, 265, 1448, 1994). Their experimental results revealed that most of the recombinant viruses even after a single passage lost the introduced vaccine gene, and none of the progeny virus after 6 passages has been found to have full-length exogeneous insert in RT-PCR experiment.

(4) In 1996, Andino and his colleagues also reported recombinant Mahoney virus expressing preS (118aa, 54aa) and core (155aa) proteins of hepatitis B virus using the same Mahoney vector (Yim et al., Virology, 218, 61, 1996). Even though they have stated that these chimeric viruses were genetically stable during the passages until the sixth progeny, their RT-PCR experimental result showed that the amounts of recombinant virus maintaining preS gene (118 aa) were markedly reduced during the fifth passage. On the other hand, their report revealed that the recombinant virus expressing a small preS protein coding 55aa residues had a markedly reduced replication capacity as compared with that of wild-type or other recombinant Mahoney strains. The result suggests that the replication capacity of recombinant chimeric viruses is not so much tightly associated with the size of the inserted vaccine gene as expected. These experimental results lead us to conclude that the biological characteristics of the recombinant chimeric virus depends on several combined factors like the size of gene inserts, characteristics of the vial vector, introduced vaccine genes, etc.

(5) Andino et al., accepting the problems of their Mahoney vector as mentioned above, developed a new Mahoney vector (MoV-2.1) by inserting a multiple cloning site and 2A-protease cleavage site at P1/P2 junction of Mahoney polyprotein cDNA (Tang et al., J. Virol., 71, 7841–7850, 1997). This MoV-2.1 vector was employed to construct recombinant chimeric virus expressing SIV gag genes (p17 or p27) or env genes (gp130 or gp41). These recombinant chimeric viruses have the similar replication capacity to that of wild type Mahoney, and express the introduced vaccine gene efficiently. However, the MoV-2.1 vector still has a problem of genetic instability. Over 99% of the recombinant chimeric viruses lose the introduced vaccine genes within the third passage. They thought that the sequence deletion during the passages was to be due to the homologous recombination between the repeated sequences at the newly introduced multiple cloning sites. They have reduced the sequence homology by 37% at the repeated sequence of Mov-2.1 vector by performing silent mutation to change the sequence without affecting amino acid sequence, and then named it MoV-2.11. They have constructed the recombinant chimeric virus Sp27(MoV-2.11) by cloning SIV p27 gene into the manipulated Mahoney vector (MoV-2.11). For the recombinant virus without silent mutation [Sp27(MoV-2.1)], 20–30% of the plaques maintained the cloned vaccine gene after first passage and none of the plaques after third passage carried the cloned gene. On the other hand, for the recombinant virus with silent mutation at the repeated sequence [Sp27(Mo-2.11)], more than 90% of the single-passaged plaques maintained the cloned gene (gag) and 30–50% of the plaques expressed the SIV gene product at third passage. Nevertheless, the Mahoney vector MoV-2.11 still has a problem of genetic instability during the passages, even though they have some progress to increase genetic stability of Mahoney vector by reducing sequence homology. According to their experimental results, the population of insert-maintaining progeny viruses was markedly reduced as passage goes on even within three passages; first (90%), second (50–70%), and third (30–50%). That means that the insert-maintaining recombinant, chimeric Mahoney virus will be rapidly diluted out among the total population if passaged little bit further.

Considering several limitations of Mahoney vectors developed by Andino group, the Mahoney vector can not be allowed as a model system for the poliovirus-mediated mucosal vaccine vector.

Therefore, it is highly recommended to develop a new model system for poliovirus-mediated mucosal vaccine vectors, which is able to overcome the limitations shown in Mahoney vectors. For that purpose, the new vector should meet the following requirements: (1) viral vector should be safe to human beings; (2) recombinant virus should be replicable, and have equivalent replication capacity to that of wild type; and (3) the introduced vaccine genes should be stably maintained during the viral passages.

SUMMARY OF THE INVENTION

An object of the present invention is to provide a replication-competent recombinant Sabin 1 poliovirus vector that is useful as a live viral vaccine vector for the development of mucosal vaccines.

Another object of the present invention is to provide a chimeric poliovirus expressing several vaccine genes cloned into the multiple cloning site of the recombinant Sabin 1 poliovirus.

The present invention provides a replication-competent recombinant Sabin 1 poliovirus vector having nongenomic sequences coding for multiple cloning site and 3C-protease cleavage site between the first amino acid and second amino acid of long polyprotein of Sabin 1 poliovirus cDNA.

The present invention further provides a replication-competent chimeric Sabin 1 poliovirus expressing exogenous vaccine genes, respectively, and their recombinant cDNA plasmids, where which have exogenous vaccine genes, respectively, at the multiple cloning site of the above-mentioned replication-competent recombinant Sabin 1 poliovirus vector.

The objects mentioned above, other features and applications of the present invention would be much more apparent by those of ordinary skills in the art from the following explanation in detail.

BRIEF DESCRIPTION OF THE DRAWINGS

FIG. 2 is a schematic representation of recombinant vectors, pTZ-PVS-3m and pTZ-PVS-4m, derived from Sabin 1 poliovirus cDNA, which have a multiple cloning site (SEQ ID NOS: 3 and 22–24) and 3C-protease cleavage site (SEQ ID NOS: 10 and 25–27), respectively.

Lane 1: HeLa cell lysate

Lane 2: Recombinant poliovirus PVS-3m-infected HeLa cell lysate

Figure 13:
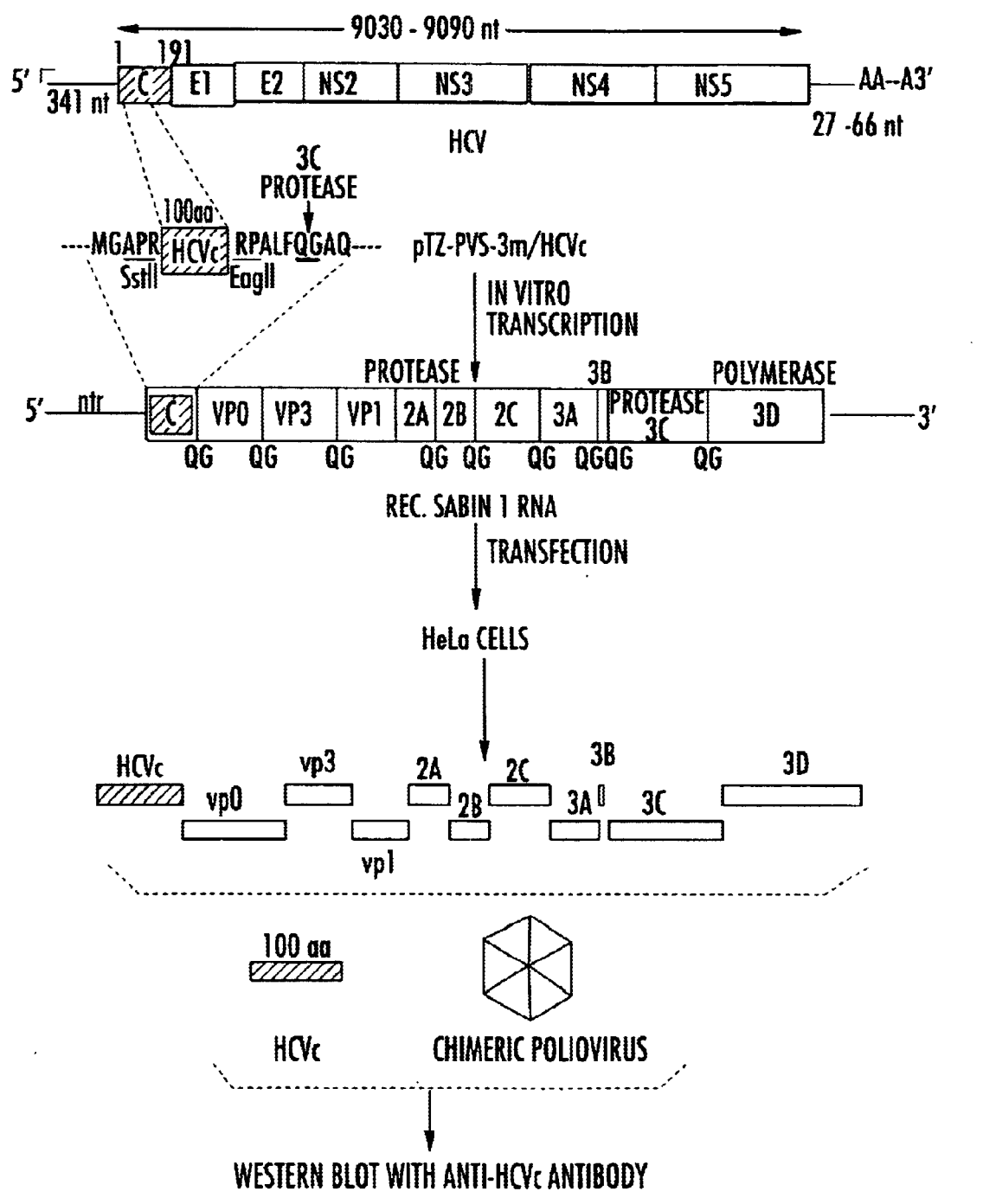

Lane 3: Cell lysate of third(3rd)-passaged chimeric poliovirus PVS-3m/env-infected HeLa cell Lane 4: Cell lysate of sixth(6th)-passaged chimeric poliovirus PVS-3m/env-infected HeLa cell Lane 5: Cell lysate of ninth(9th)-passaged chimeric poliovirus PVS-3m/env-infected HeLa cell Lane 6: Cell lysate of twelveth(12th)-passaged chimeric poliovirus PVS-3m/env-infected HeLa cell FIG. 13 is a schematic representation of the procedures for construction of chimeric poliovirus PVS-3m/HCVc by cloning HCV core gene into multiple cloning site (SEQ ID NO: 28) of recombinant plasmid pTZ-PVS-3m and its expression of the HCV core protein.

Figure 14:
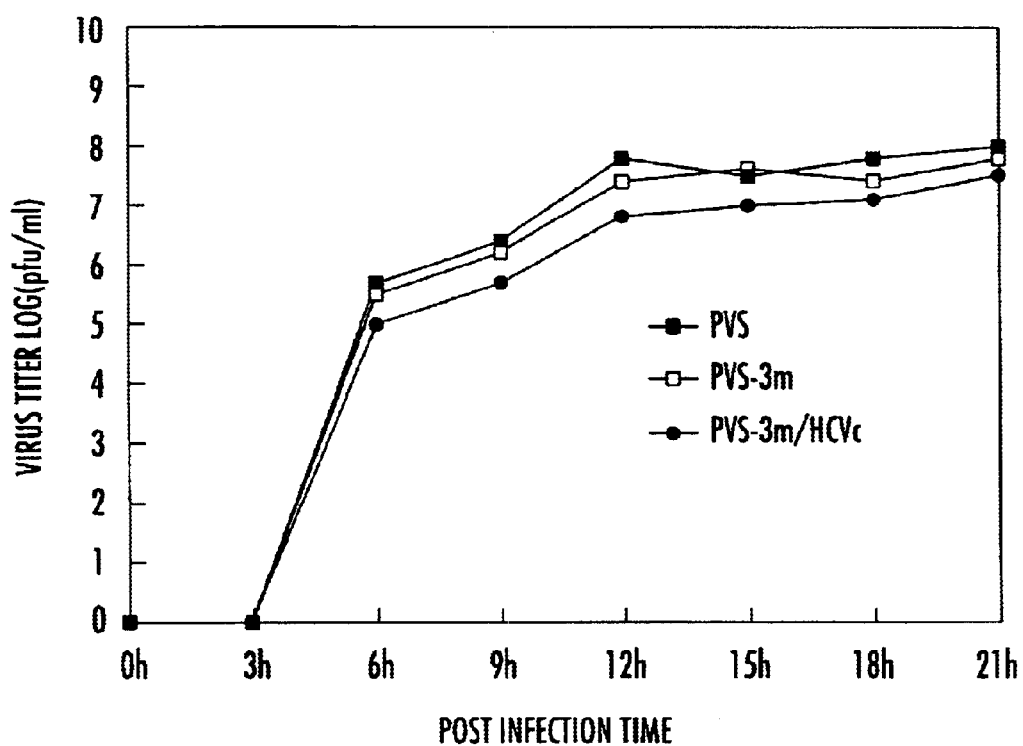

FIG. 14 shows one-step growth curve to evaluate the replication capacity of chimeric poliovirus PVS-3m/HCVc. Titer of virus in the culture supernatant was determined every 3 hrs by TCID50 and plaque assay.

Figure 15:
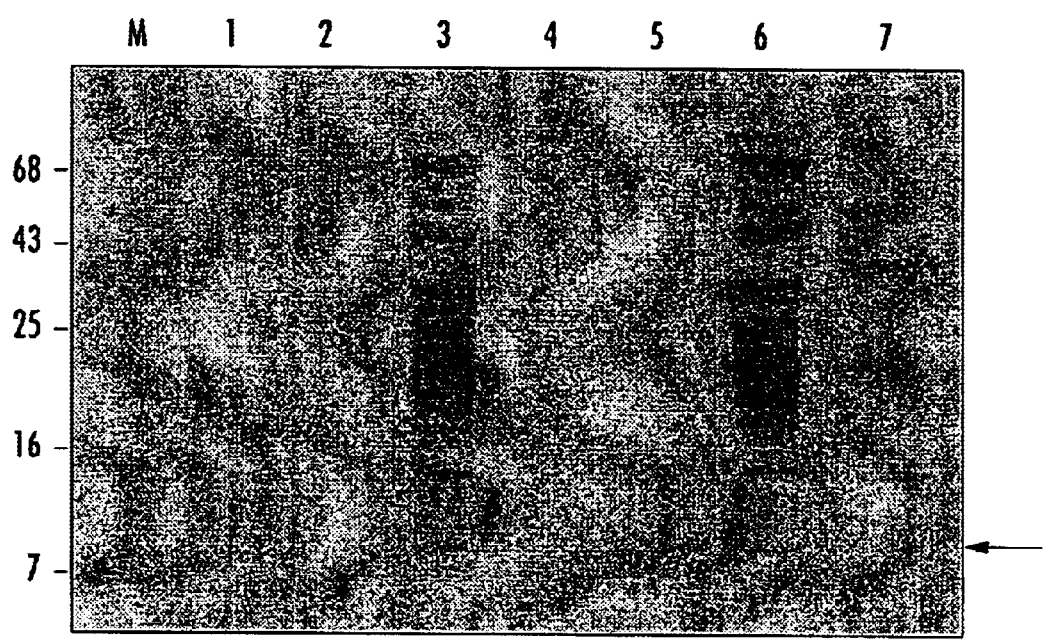

FIG. 15 is the western blot of HCV core protein to check the expression patterns of HCV core protein when HeLa cells are infected with chimeric poliovirus PVS-3m/HCVc:

Lane 1: HeLa Cell lysate

Lane 2: Wild Sabin type 1 poliovirus-infected HeLa cell lysate

Lane 3: Chimeric poliovirus PVS-3m/HCVc-infected HeLa cell lysate

Lane 4: Pellet of chimeric poliovirus PVS-3m/HCVc

Lane 5: Culture supernatant concentrate of virus-free HeLa cell

Lane 6: Pellet of chimeric poliovirus PVS-3m/HCVc-infected HeLa cell lysate

Figure 16:
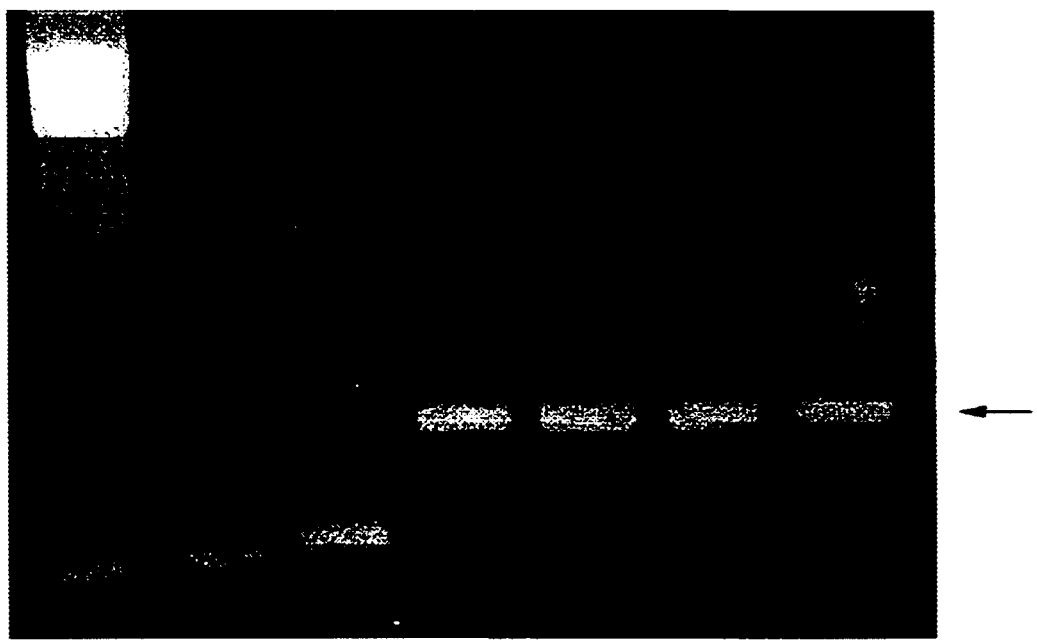

Lane 7: Supernatant of chimeric poliovirus PVS-3m/HCVc-infected HeLa cell lysate FIG. 16 represents the PCR analysis of the HCV core protein gene, cloned in the chimeric virus, up to 12th passage to evaluate the genetic stability of chimeric poliovirus PVS-3m/HCVc during the passages:

Lane 1: PCR product from wild-type Sabin 1 poliovirus-infected HeLa cell

Lane 2: PCR product from recombinant poliovirus PVS-3m-infected HeLa cell

Figure 17:
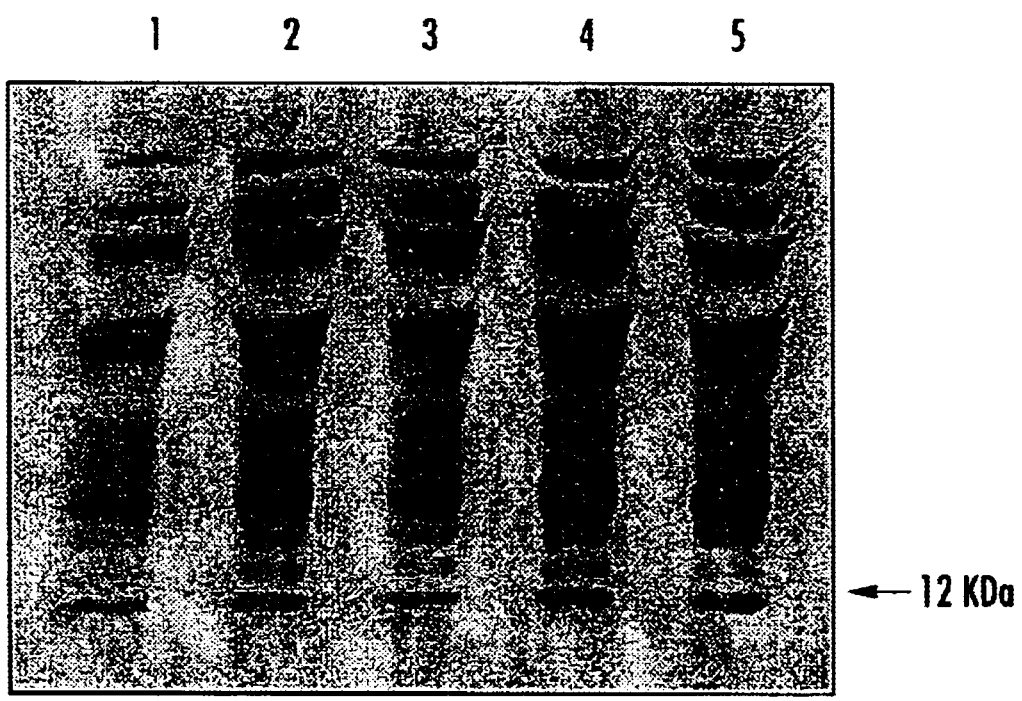

Lane 3: PCR product from the third(3rd)passaged chimeric poliovirus PVS-3m/HCVc-infected HeLa cell Lane 4: PCR product from the sixth(16th)-passaged chimeric poliovirus PVS-3m/HCVc-infected HeLa cell Lane 5: PCR product from the ninth(9th)-passaged chimeric poliovirus PVS-3m/HCVc-infected HeLa cell Lane 6: PCR product from the twelveth(12th)-passaged chimeric poliovirus PVS-3m/HCVc-infected HeLa cell FIG. 17 is the western blot of HCV core protein, expressed from the chimeric poliovirus, up to 12th passage in order to evaluate the expression stability of chimeric poliovirus PVS-3m/HCVc during the passages:

Lane 1: Cell lysate of first(1st)-passaged chimeric poliovirus PVS-3m/HCVc-infected HeLa cell Lane 2: Cell lysate of third(3rd)-passaged chimeric poliovirus PVS-3m/HCVc-infected HeLa cell Lane 3: Cell lysate of sixth(6th)-passaged chimeric poliovirus PVS-3m/HCVc-infected HeLa cell Lane 4: Cell lysate of ninth(9th)-passaged chimeric poliovirus PVS-3m/HCVc-infected HeLa cell Lane 5: Cell lysate of twelveth(12th)-passaged chimeric poliovirus PVS 3m/HCVc-infected HeLa cell

DETAILED EXPLANATION OF THE INVENTION

Poliovirus, belonging to the Picornaviridae family, is a causative agent of poliomyelitis by infecting and destroying the central nervous system (Bodian and Howe, 1955; Couderc et al., 1989). Poliomyelitis has been effectively controlled by the use of inactivated or live attenuated vaccines. Three serotypes of attenuated strains have been selected by numerous passages of wild-type strains in monkey tissues in vivo and in vitro (Sabin and Boulger, J. Biol. Stand.,1,115 1973). These strains (Sabin 1, 2, and 3), which replicate in the primate gut and induce a strong mucosal and systemic immunity, have shown a good safety record. However, 5–10 cases of vaccine-associated poliomyelitis (VAP) was reported to occur every year in the United States after immunization with oral poliovirus (OPV) (Ogra and Faden, J. Pediatr., 108.1031, 1986; Nkowane et al., JAMA, 257, 1335, 1987). VAP may result from the genetic variation of the Sabin strain, such as recombination (Furione et al., Virology, 196, 199, 1993) or point mutation (Guillot et al., Vaccine, 12, 503, 1994). Indeed, vaccine-derived neurovirulent strains are found in the gut of healthy vaccines and in the central nervous system of patients with VAP (Georgescu et al., J. Virol., 68, 8089, 1994; Friedrich, Acta Virol., 40, 157, 1996). However, VAP has been reported to be most frequently associated with Sabin 2 and 3, but rarely with Sabin 1 (Furione et al., Virology, 196, 199,1993; Otelea et al, Dev. Biol. Stand., 78, 33, 1992). The greater number of attenuating mutations in Sabin 1 is probably reflected in the higher safety of this strain in comparison with type 2 and 3 strains. The Sabin 1 strain of poliovirus, therefore, is the best candidate for a live viral vector to deliver foreign antigens to the enteric tract when mucosal immunity is desired for protection of infectious disease.

The present invention is based on these advantages of Sabin type 1 strain.

The inventors have made an effort to use Sabin type 1 strain of poliovirus as a mucosal vaccine vehicle. They constructed a recombinant plasmid pTZ-PVS-3m by introducing a multiple cloning site and 3C-protease cleavage site into N-terminal end of the cDNA of Sabin 1 poliovirus. RNA transcript synthesized from the plasmid was infectious when transfected into HeLa cells, resulting in production of recombinant progeny virus (PVS-3m). The recombinant virus has a slightly reduced replication capacity of 1–10 times as lower as that of wild type Sabin. Nevertheless, chimeric Sabin 1 polioviruses, obtained by transfection as mentioned above after cloning various vaccine genes into the vector pTZ-PVS-3m, maintain the foreign genes to be expressed stably at least up to 12 serial passages.

The Sabin type 1 strain of poliovirus was developed in 1961 by Sabin and his colleagues. They developed an attenuated, less neurovirulent and much more immunogenic poliovirus vaccine strain through sequential passages of wild-type Mahoney strain in the established cell line of monkey kidney cells, and then called Sabin 1 poliovirus vaccine strain. Sabin 1 has 57 nucleotide substitutions in comparison, with wild type Mahoney strain, 21 of which cause amino acid substitution. The nucleotide sequence of Sabin type 1 strain is shown as SEQ. ID. NO. 1. All of the coding-change alterations are concentrated on the N-terminal half region of VP1 major outer capsid protein (Kitamura et al., Nature, 291, 547–553, 1981; Nomoto et al., Proc. Natl. Acad. Sci. USA, 79, 5793–5797, 1982). Replication capacity of Sabin 1 strain is 2–3 log lower than that of wild-type Mahoney strain. Since it has lost neurotropism during the passages, it does not cause paralytic poliomyelitis in primates. Nevertheless it still maintains the enterotropic capacity enough to induce a potent mucosal and systemic immunity. It was first approved as an oral polio vaccine (OPV) in the United States in 1961 and came into general use by 1963 (Ogra et al., Rev. Inf. Diseases 2, 352–369, 1980).

Figure 1:
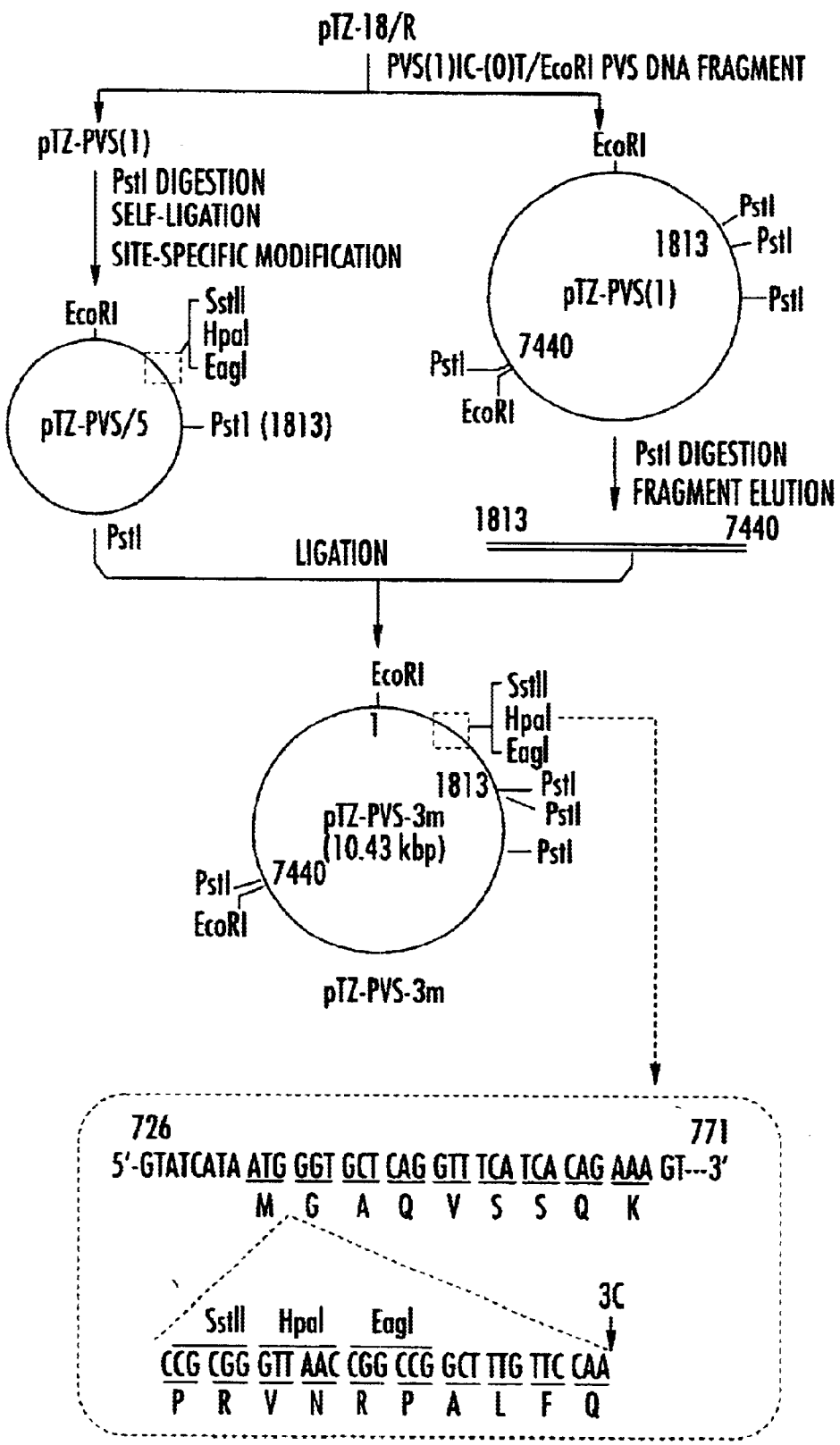
FIG. 1 is a schematic representation for the construction of a recombinant plasmid Ptz-PVS-3m in order to achieve the present invention. The multiple cloning site (SEQ ID NOS: 3 and 22–24) is also shown.

For the present invention, multiple cloning site and 3C-protease cleavage site are newly introduced between the first and second amino acids of Sabin 1 long polyprotein cDNA by site-specific insertion experiments in order to construct recombinant plasmid pTZ-PCV-3m (FIG. 1). The multiple cloning site is designed to have three restriction sites of SstII, HpaI and EagI.

Figure 3:
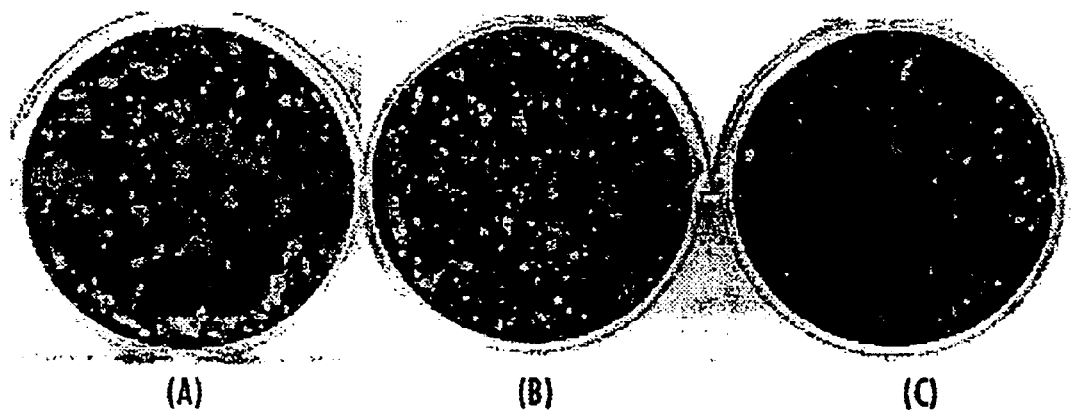
FIG. 3 is photograph showing that the wild type and recombinant poliovirus cDNAs are able to produce progeny viruses when trsfected into HeLa cells. HeLa cells were tranfected with RNA transcript synthesized from wild-type cDNA (A), with RNA transcript synthesized from recombinant plasmid pTZ-PVS-3m (B), or with RNA transcript synthesized from recombinant plasmid pTZ-PVS-4m (C).
Figure 5:
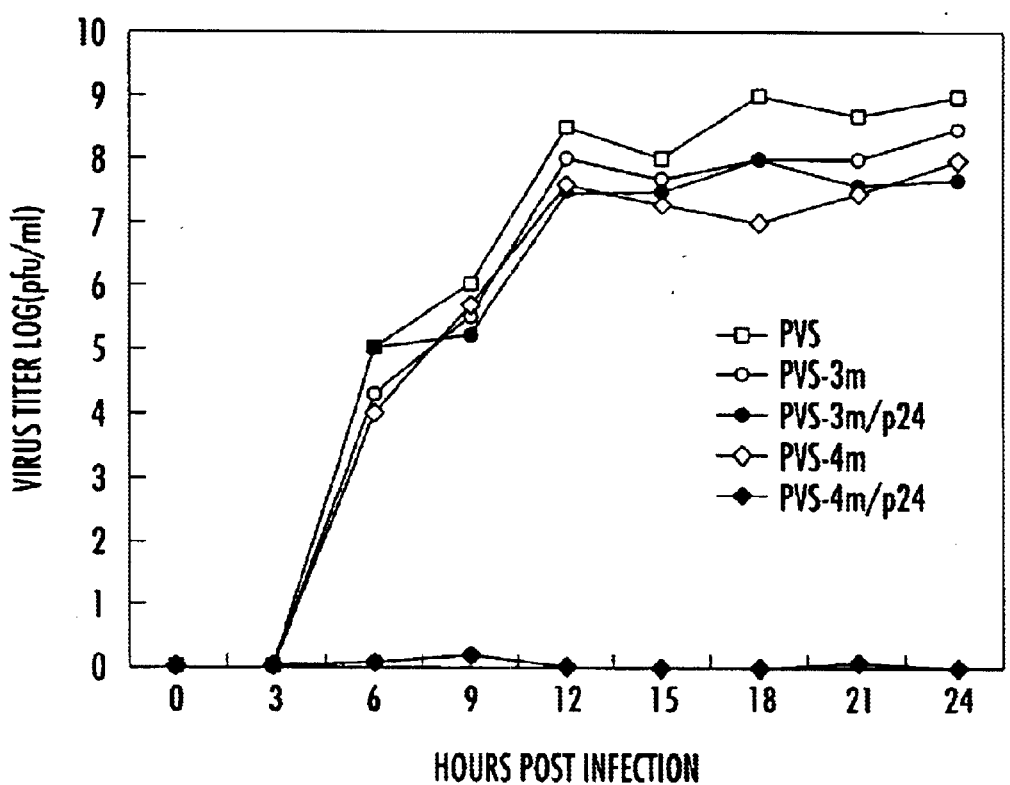
FIG. 5 shows one-step growth curve to evaluate the replication capacity of the wild type and recombinant Sabin 1 poliovirus. Titer of virus in the culture supernatant was determined every 3 hrs by TCID50 and plaque assay.

Recombinant plasmid pTZ-PCV-3m was the most effective for production of recombinant progeny virus, when transfected into HeLa cell monolayers with its RNA transcript, among the several recombinant plasmids containing exogeneous multiple cloning site and 3C-protease cutting site at different positions of poliovirus. (FIG. 3). One-step growth curve plotted by measuring virus titer through the $TCID_{50}$ assay and plaque assay reveals that the replication capacity of recombinant poliovirus PCV-3m is at most 1 log lower than that of the wild-type Sabin 1 strain, while is the highest among the various chimeric polioviruses (FIG. 5).

Figure 4:
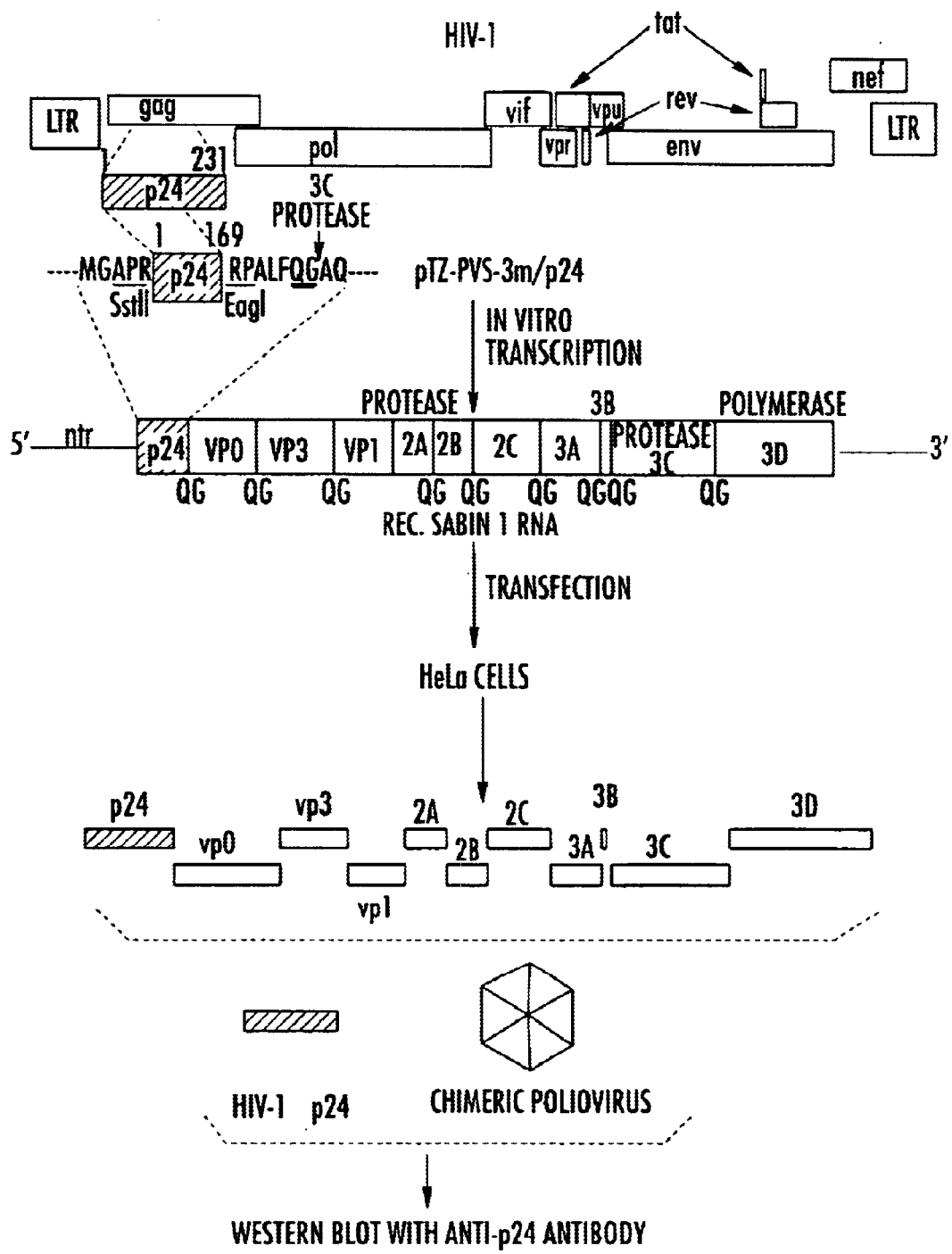
FIG. 4 is a schematic representation of the procedure for production of chimeric poliovirus PVS-3m/p24 by inserting HIV-1 p24 gene into the multiple cloning site (SEQ ID NO: 28) of recombinant plasmid pTZ-PVS-3m, and expression of HIV-1 p24 protein.
Figure 10:
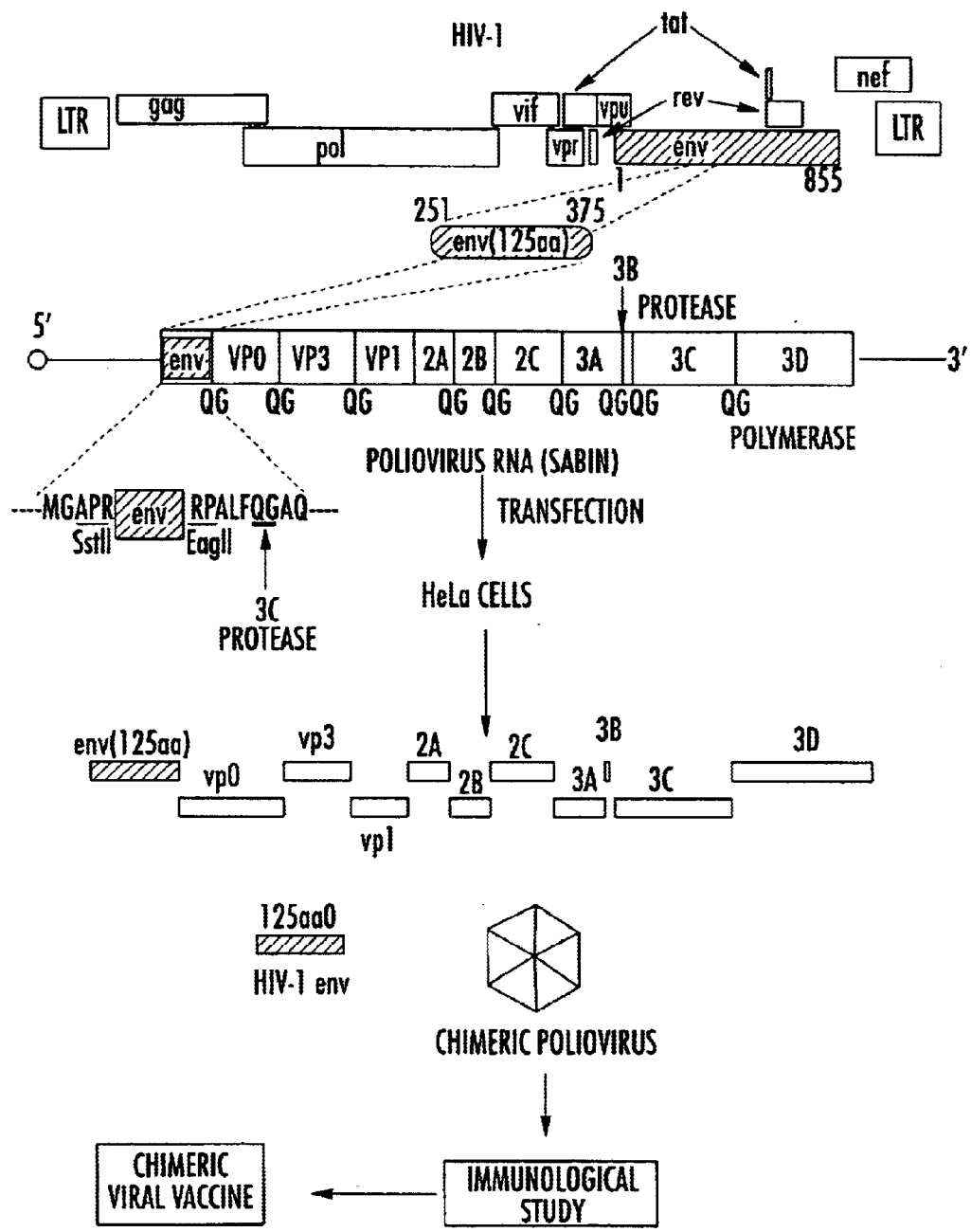
FIG. 10 is a schematic representation of the procedures for construction of chimeric poliovirus PVS-3m/env by cloning HIV-1 envelope glycoprotein gene env(125aa) into multiple cloning site (SEQ ID NO: 28) of recombinant plasmid pTZ-PVS-3m and its expression of the HIV-1 envelope glycoprotein.

In the present invention, three exogenous vaccine genes, HIV-1 p24 (169aa), HIV-1 env (125aa) and HCV core gene (100aa) were successfully introduced into the multiple cloning site of pTZ-PCV-3m, resulting in production of chimeric poliovirus PCV-3m/p24, PCV-3m/env and PCV-3m/HCVc, respectively, when their RNA transcripts were transfected into HeLa cells (FIG. 4, FIG. 10 and FIG. 13).

Figure 6:
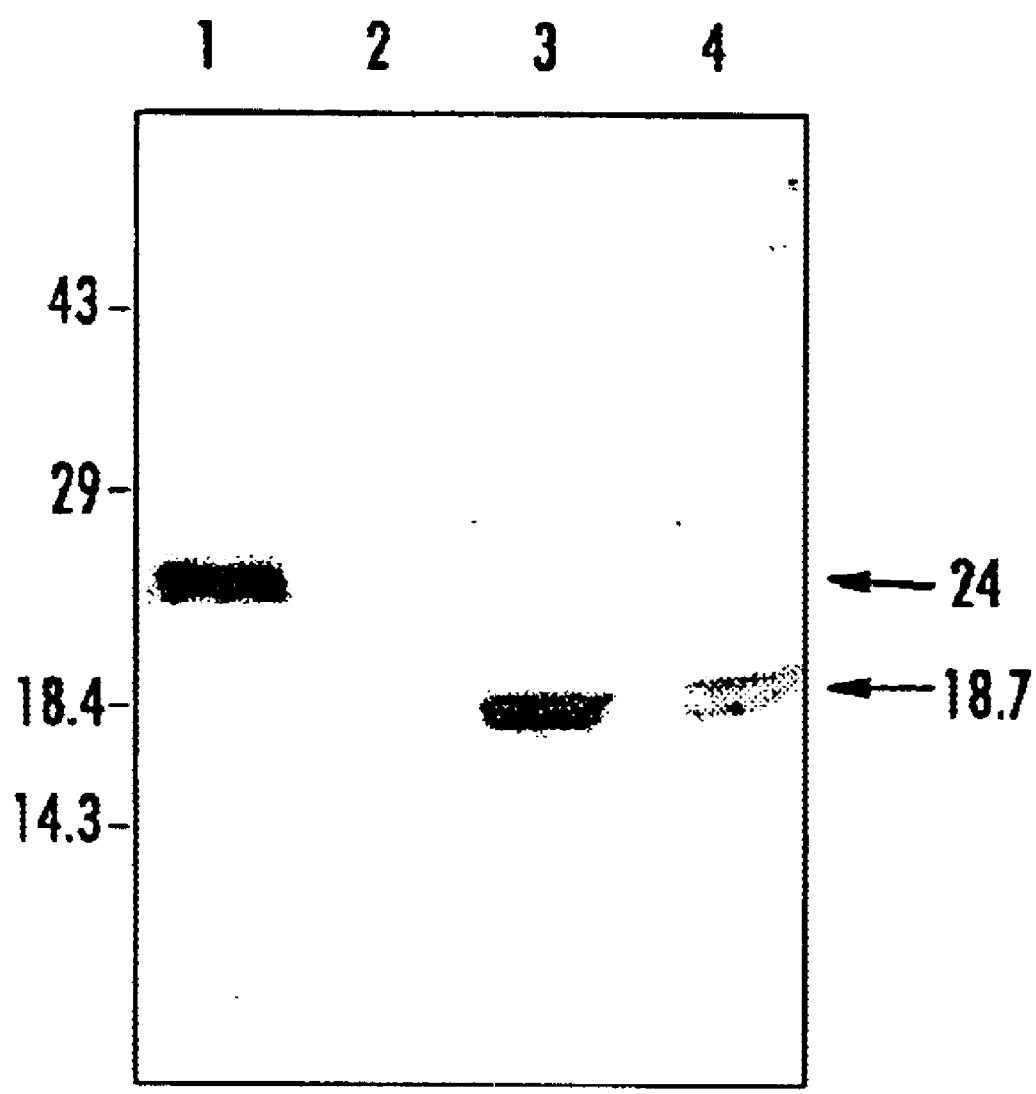
FIG. 6 is the western blot of HIV-1 p24 protein expressed in culture supernatant and HeLa cells infected with chimeric poliovirus PVS-3m/p24:
  Lane 1: HIV-1/-tat (tat defective HIV-1 strain; supplied from Dr Sodroski, Dana-Farber Cancer Ins., US)
  Lane 2: Control (wild type Sabin 1 poliovirus-infected HeLa cell lysate)
  Lane 3: Chimeric poliovirus PVS-3m/p24-infected HeLa cell lysate
  Lane 4: Culture supernatant of chimeric poliovirus PVS-3m/p24-infected HeLa cell
Figure 7:
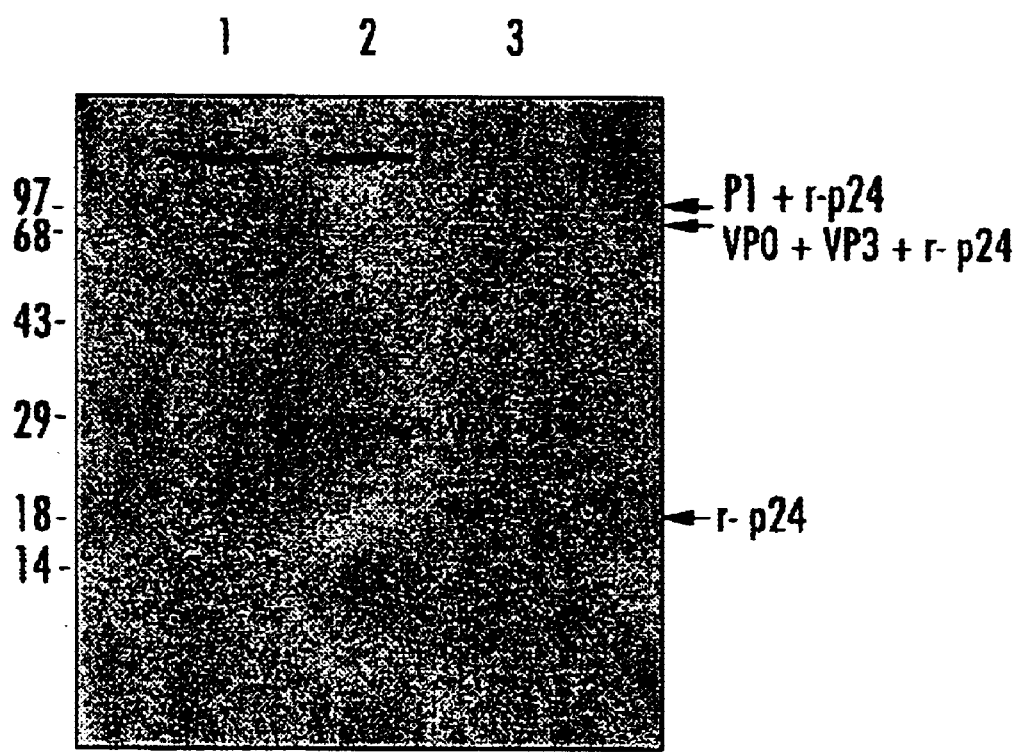
FIG. 7 is the results of radioimmunoprecipitation to evaluate the antigenecity of HIV-1 p24 protein expressed from the chimeric poliovirus PVS-3m/p24:
  Lane 1: Non-infected cell lysate
  Lane 2: Wild type Sabin 1 poliovirus-infected HeLa cell lysate
  Lane 3: Chimeric poliovirus PVS-3m/p24-infected HeLa cell lysate
Figure 11:
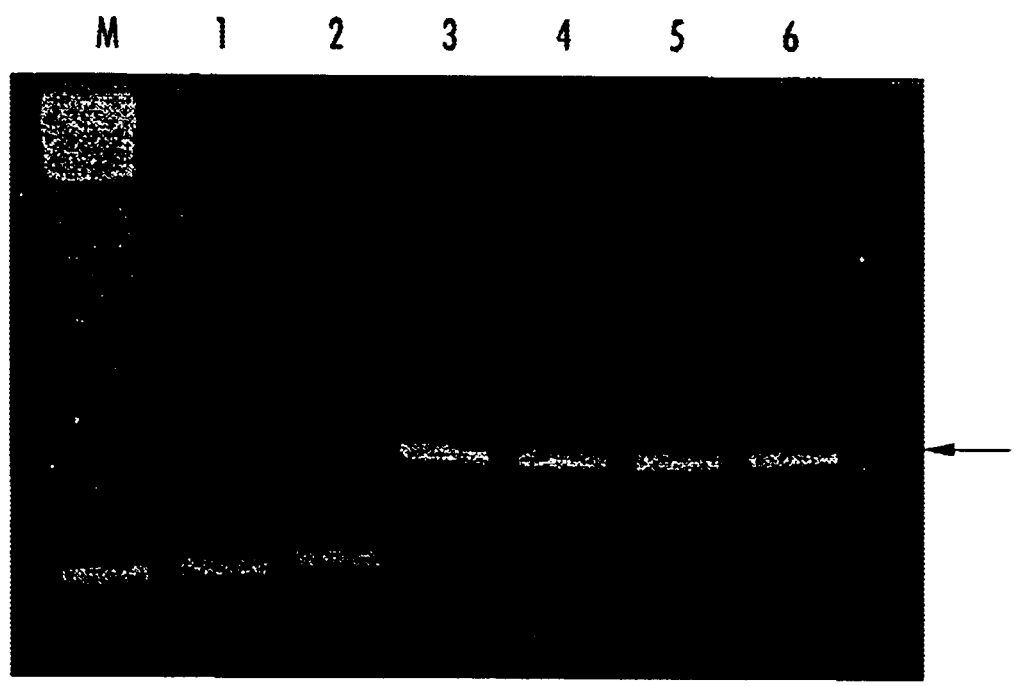
FIG. 11 represents the PCR analysis of HIV-1 env gene, cloned in chimeric poliovirus, up to 12th passage to evaluate the genetic stability of chimeric poliovirus PVS-3m/env during the passages:
  Lane 1: PCR product from wild-type Sabin 1 poliovirus-infected HeLa cell
  Lane 2: PCR product from recombinant poliovirus PVS-3m-infected HeLa cell
  Lane 3: PCR product from the third(3rd)-passaged chimeric poliovirus PVS-3m/env-infected HeLa cell
  Lane 4: PCR product from the sixth(6th)-passaged chimeric poliovirus PVS-3m/env-infected HeLa cell Lane 5: PCR product from the ninth(9th)-passaged chimeric poliovirus PVS-3m/env-infected HeLa cell Lane 6: PCR product from the twelfth(12th)-passaged chimeric poliovirus PVS-3m/env-infected HeLa cell
Figure 12:
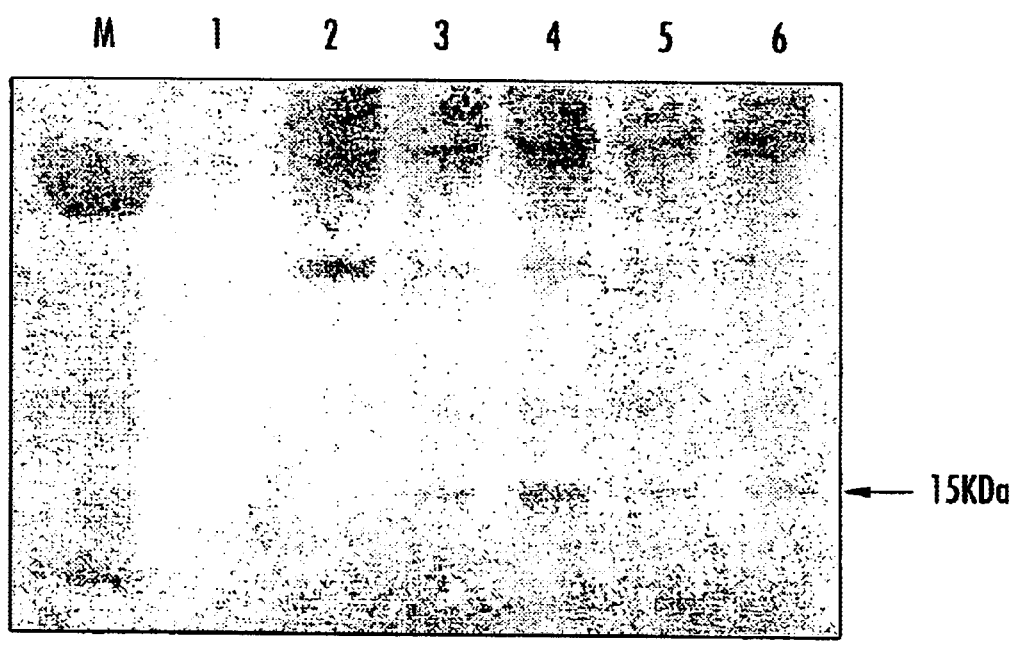
FIG. 12 is the western blot of HIV-1 env protein, expressed from the chimeric poliovirus, up to 12th passage in order to evaluate the expression stability of chimeric poliovirus PVS-3m/env during the passages.

These chimeric polioviruses effectively express the exogenous protein during the replication in HeLa cells (FIG. 6 and FIG. 15), and the expressed proteins maintain the original antigenecity (FIG. 7). Moreover, these chimeric polioviruses are genetically stable during the serial passages (FIG. 8, FIG. 11 and FIG. 16), and the expression of foreign genes is not damaged during the passages (FIG. 9, FIG. 12 and FIG. 17).

These results strongly suggest that the recombinant plasmid pTZ-PCV-3m can be used as an effective vaccine vector for the development of several mucosal vaccines against several infectious diseases. The recombinant plasmid pTZ-PCV-3m of the present invention has been deposited at the Korea Collection of Type Cultures (KCTC) in Korea Research Institute of Bioscience and Biotechnology (KRIBB) lacated in Taejon on Aug. 6, 1997 with the accession number of KCTC-0365BP.

The exogenous vaccine genes which can be introduced into the multiple cloning site of the recombinant plasmid pTZ-PVC-3m of the present invention may include those derived from various infectious viruses, such as HIV, HBV, HCV, human papillomavirus, rotavirus etc, but not limited thereto.

The recombinant poliovirus plasmids containing several exogenous vaccine genes will be transfected into host cells, such as HeLa cell, by known methods to obtain chimeric polioviruses, which will be used as oral vaccines.

Free Texts in Sequence Listing

SEQ.ID.NO. 2 is an artificial sequence which is a synthetic sequencing primer for DNA amplification having multiple cloning site and 3C-protease cleavage site:

SEQ.ID.NO. 3 is an artificial sequence which is a peptide coded by SEQ. ID. NO. 2:

SEQ.ID.NO. 4 is an artificial sequence which is a primer for DNA amplification having multiple cloning site and 3C-protease cleavage site:

SEQ.ID.NO. 5 is an artificial sequence which is a peptide coded by SEQ. ID. NO. 4:

SEQ.ID.NO. 6 is an artificial sequence which is a primer for DNA amplification having multiple cloning site and 3C-protease cleavage site:

SEQ.ID.NO. 7 is an artificial sequence which is a primer for DNA amplification having multiple cloning site and 3C-protease cleavage site:

SEQ.ID.NO. 8 is an artificial sequence which is a peptide coded by SEQ. ID. NO. 7:

SEQ.ID.NO. 9 is an artificial sequence which is a primer for DNA amplification having multiple cloning site and 3C-protease cleavage site:

SEQ.ID.NO. 10 is an artificial sequence which is a peptide coded by SEQ. ID. NO. 9:

SEQ.ID.NO. 11 is an artificial sequence which is a SstII-sense primer for DNA amplification having multiple cloning site and 3C-protease cleavage site:

SEQ.ID.NO. 12 is an artificial sequence which is a EagI-antisense primer for DNA amplification having multiple cloning site and 3C-protease cleavage site:

SEQ.ID.NO. 13 is an artificial sequence which is a cDNA synthesis primer:

SEQ.ID.NO. 14 is an artificial sequence which is a sense primer for DNA amplification having multiple cloning site and 3C-protease cleavage site:

SEQ.ID.NO. 15 is an artificial sequence which is an antisense primer for DNA amplification covering nucleotide 797–814 of Sabin 1 poliovirus:

SEQ.ID.NO. 16 is an artificial sequence which is a SstII-sense primer for PCR

SEQ.ID.NO. 17 is an artificial sequence which is a EagI antisense primer for DNA amplification:

SEQ.ID.NO. 18 is an artificial sequence which is a sense primer for DNA amplification:

SEQ.ID.NO. 19 is an artificial sequence which is an antisense primer for DNA amplification: and SEQ.ID.NO. 20 is an artificial sequence having multiple cloning site and 3C-protease cleavage site.

EXAMPLES

The present invention will be described in more detail by way of various examples, which should not be construed to limit the scope of the present invention.

Example 1

Construction of Recombinant Plasmid pTZ-PCV-3m

Plasmid PVS(1)IC-(0)T (Poliovirus Sabin 1 cDNA plasmid; obtained by courtesy from Dr. Nomoto at Tokyo University) was digested with restriction enzyme EcoRI and cDNA was isolated. The cDNA was cloned into EcoRI site of plasmid pTZ-18/R (Pharmacia) to construct plasmid pTZ-PVS(1).

Plasmid pTZ-PVS(1) was digested with restriction enzyme PstI to reduce the size of cDNA part and subjected to self-ligation to produce plasmid subclone pTZ-PVS(1)/5 having the nucleotide sequence 1–1813 of the poliovirus cDNA.

Plasmid pTZ-PVS(1)/5 was transformed into *E. coli* CJ236($dut^-$, $ung^-$, $C^{mr}$) and the transformant was cultured in LB-amp chloramphenicol medium (LB, 40 μg/ml ampicillin, 30 μg/ml chloramphenicol) supplemented with 0.25 μg/ml of uridine. When the OD600 nm of the culture reaches about 0.5–0.6, cells were super-infected with more than 10 moi/bacterium of M13K07 helper phage (Pharmacia), and then further cultured for about 8 more hours in LB-amp chloramphenicol medium supplimented with kanamycin, thymidine and uridine to obtain uracil-incorporated single-stranded phagemid.

The phagemid was precipitated with PEG/NaCl (20% PEG and 2.5M NaCl in DDW) and extraced with phenol/chloroform to have ss-DNA.

One (1) μg of the ss DNA and 5 pmole of mutagenic primer having the sequence shown as SEQ. ID. NO. 2 were added into 10 ul of buffer (2 mM $MgCl_2$, SOnM NaCl in 20 mM Tris-HCl: pH 7.4) and incubated at a water bath of 70° C. for 10 minutes followed by annealing through gradually cooling to 30° C.

One (1) μl of 10× synthesis buffer (5 mM of each dNTP, 10 mM of rATP, 100 mM of Tris-HCl: pH 7.4, 50 mM of $MgCl_2$, 20 mM of DTT), 3 units of T4 DNA ligase (Bio-Rad) and 1 unit of T4 DNA polymerase (Bio-Rad) were added and allowed to react on ice for 5 minutes, 25° C. for 5 minutes, and then 37 C for 90 minutes, sequentially.

Synthesized ds-DNA was transformed into *E. coli* MV1190 ($dut^+$, $ung^+$, $C^{mr}$) and screened for those having restriction sites of SstII, HpaI, and EagI by digestion with these enzymes. cDNA fragment (covering nucleotide 1814–7440) obtained by digesting plasmid pTZ-PVS(1) with PstI was ligated into corresponding PstI site of the manipulated plasmid pTZ-PVS(5)/m to produce recombinant plasmid pTZ-PVS-3m. Recombinant vector pTZ-TVS (5)/m has 3C-protease cleavage site(AXFQ/G; SEQ ID NO: 29) (Dougherty and Semler, Microbiological Rev. 57, 781–822, 1993) and multiple cloning site (SstII-HpaI-EagI) at the junction between the first and the second amino acids of long polyprotein of poliovirus Sabin 1 cDNA. Newly inserted region has the amino acid sequence of SEQ. ID. NO. 3.

Comparative Example 1

Construction of Recombinant Vector pTZ-PVS-m

By following the same procedure in Example 1 except using a different mutagenic primer having the sequence of SEQ. ID. NO. 4, recombinant plasmid pTZ-PVS-m was constructed.

Recombinant vector pTZ-PVS-m has 3C-protease c ie d multiple cloning site (SstII-HpaI-EagI) at the junction of the third and the fourth amino acids of N-terminal of poliovirus Sabin 1 cDNA. Newley inserted region has the amino acid sequence of SEQ. ID. NO. 5. This vector was designed to have N-terminal of viral polyprotein begins with GG - - - , with expecting myristoylation site preserved during the 3C-mediated proccessing.

Comparative Example 2

Construction of Recombinant Vector pTZ-PVS-2m

By following the same procedure in Example 1 except using different mutagenic primer having the sequence of SEQ. ID. NO. 6, recombinant vector pTZ-PVS-2m was constructed.

Recombinant vector pTZ-PVS-2m is similar to pTZ-PVS-m of Comparative Example 1 except having one guanine(G) instead of two at N-terminal of viral polyprotein during the 3C-mediated processing.

Comparative Example 3

Constriction of Recombinant Plasmid pTZ-PVS-2m/1

By following the same procedure in Example 1 except two points, that the recombinant plasmid pTZ-PVS-2m of Comparative Example 2 was used for mutagenic template and different mutagenic primer having the sequence of SEQ. ID. NO. 7 was used, recombinant plasmid pTZ-PVS-2m/1 was constructed.

Recombinant plasmid pTZ-PVS-2m/1 was designed to have a lower G/C content in the multiple cloning site than the plasmid pTZ-PVS-m in Comparative Example 1 or plasmid pTZ-PVS-2m in Comparative Example 2 by replacing some portion of G/C with A/T. And, the multiple cloning site was changed to SstII-HpaI-XhoI and the newley inserted region has amino acid sequence of SEQ. ID. NO. 8.

Comparative Example 4

Construction of Recombinant Vector pTZ-PVS4m

By following the same procedure in Example 1 except using different mutagenic template and mutagenic primer having the sequence of SEQ. ID. NO. 9, recombinant vector pTZ-PVS-4m was constructed.

Recombinant vector pTZ-PVS4m has 3C-protease cleavage site and multiple cloning site (ApaI-HpaI-XhoI) at the junction site between VP3 and VP1 of long polyprotein of Sabin 1 poliovirus cDNA. Newley inserted exgeneous region has amino acid sequence of SEQ. ID. NO. 10.

Example 2

Infectivity of the RNA Transcripts Synthesized from the Recombinant Poliovirus Plasmids The plasmids in Example 1 and Comparative Examples 1–4 were linealized by SalI digestion and subjected to in vitro transcription to synthesize RNA transcripts as described previously (Bae et al., Nucleic Acid Res., 21, 2703, 1993).

The RNA transcript (0.1 μg) was transfected into monolayered HeLa cells grown in DMEM medium (GIBCO/BRL) supplemented with 10% FCS (Fetal Calf Serum) by DEAE-Dextran method according to the vender's protocol (Stratagene Kit). Transfected cells were cultivated with methylcellulose-DMEM (prepared by adding 1.2% methylcellulose to DMEM medium supplemented with 10% FCS) at 37° C. $CO_2$ incubator for 2 days. Cells were stained with 0.1% crystal violet to observe plaques. The number of plaques as shown in Table 1 denotes transfection capacity of each RNA transcript. FIG. 3 shows the pictures of plaques produced by transfection of each RNA transcript synthesized from the recombinant plasmid.

TABLE 1

| RNA Transcript | Number of plaques |
|---|---|
| pTZ-PVS(1) | $2.0 \times 10^3$ |
| pTZ-PVS-m | 0 |

TABLE 1-continued

| RNA Transcript | Number of plaques |
|---|---|
| pTZ-PVS-2m | 0 |
| pTZ-PVS-2m/1 | <1 |
| pTZ-PVS-3m | $1.9 \times 10^3$ |
| pTZ-PVS-4m | $2.0 \times 10^2$ |

Table 1 shows that the RNA transcript from the plasmid pTZ-PVS-3m has the most potent transfection capacity among the recombinant plasmids except the wild-type strain. The recombinant plasmid pTZ-PVS-3m was deposited at Korea Collection of Type Cultures on Aug. 6, 1997 under the accession number of KCTC-0365BP.

Example 3

Construction of Chimeric Poliovirus Plasmid pTZ-PVS-3m/p24 and Production of Chimeric Poliovirus PVSS-3m/p24 cDNA fragment covering N-terminal 169 amino acid residues of HIV-1 p24 was amplified from the HIV-1 cDNA (HXB2; obtained from NIH AIDS Research and Reference Reagent Program, USA) by PCR with two p24-specific PCR primers: SstII-p24-sense primer (SEQ. ID. NO. 11) and EagI-p24-antisense primer (SEQ. ID. NO. 12) based on the sequence information published by Terwilliger et al (Proc. Natl. Acad. Sci., 86, 3857, 1989). The PCR fragment was extracted from the agarose gel, digested with SstII and EagI and then introduced into the corresponding site of the plasmid pTZ-PVS-3m of Example 1 to construct recombinant plasmid pTZ-PVS-3m/p24 as illustrated in FIG. 4.

RNA transcript synthesized from the recombinant plasmid pTZ-PVS-3m/p24 was trarsfected into the monolayered HeLa cells as described in Example 2. Transfected HeLa cells were further cultured at 37° C. $CO_2$ incubator until full cytopathic effect (CPE) was detected on the monolayered cells. The culture supernatants were harvested as a source of chimeric poliovirus PVS-3m/p24.

Example 4

One-step Growth Curve of Chimeric Poliovirus PVS-3m/p24

In order to evaluate the replication capacity of chimeric poliovirus expressing HIV-1 p24 protein, one-step growth curve was determined by measuring the virus titer of culture supernatants at each time point.

Wild-type Sabin 1 poliovirus (PVS), or recombinant or chimeric poliovirus of PVS-3m, PVS-4m, PVS-3m/p24, or PVS-4m/p24 was inoculated into HeLa cells in 60 mm plate ($4.8 \times 10^5$ cells) at 10 moi for 1 hour at room temperature so that the virus can be adhered to cells. Cells were washed with PBS and then refed with 3 ml of DMEM, followed by cultivation in 37° C. $CO_2$ incubator. After infection, the culture supernatants were taken every three hours and subjected to titration of the virus from each sample by plaque assay or $TCID_{50}$ assay as described in Virology a Practical Approach (p13 ed. by BWJ Mahy. IRL press, 1985). The results are shown in FIG. 5.

As shown in FIG. 5, the recombinant poliovirus PVS-3m is maximum 1 log lower than the wild-type Sabin 1 (PVS) in the replication capacity, while the chimeric poliovirus PVS-3m/p24 shows the similar replication capacity to thst of the recombinant poliovirus PVS-3m. Whereas, the recombinant poliovirus PVS-4m shows more than 2 log lower than the wild-type Sabin 1(PVS) in the replication capacity, and the p24-integrated plasmid pTZ-PVS-4m/p24 was unlikely to produce replication-competent chimeric poliovirus PVS-4m/p24.

Example 5

Expression Pattern of Exogenous p24 Protein During the Replication of Chimeric Poliovirus PVS-3m/p24

In order to determine whether the chimeric poliovirus PVS-3m/p24 is able to express HIV-1 p24 protein during the replication, chimeric poliovirus PVS-3m/p24 was inoculated into HeLa cells at 10 moi concentration. Six hours later, the cells were harvested, washed with PBS twice, resuspended with cell lysis buffer (80 mM NaCl, 5 mM $MgCl_2$, 10 mM Tris-Cl: pH 7.4, 1 mM DTT, 0.5% NP40), allowed to stand on ice for 5 minutes and then centrifuged to remove nucleus and cell debris. The supernatant was mixed with the equal volume of 2× sample buffer (5 mM Tris:pH 6.8, 1% β-mercaptoethanol, 10% glycerol, 0.03% bromophenol blue), boiled for 3 minutes, and then separated on a 10% SDS-PAGE. Separated samples were transblotted to a nitrocellulose membrane (Millipore) using a semi-dry transblotter (Bio-Rad) and then screened with AIDS patients' sera. The results are shown in FIG. 6.

The recombinant p24 protein (169aa) was detected at the lower band (18.4 kDa) than that of wild type p24 (24 kDa) in western blot experiment, which means that the recombinant p24 was produced by the infection of chimeric poliovirus, not by the contamination of the wild type p24. Therefore, the result shown in FIG. 6 clearly elucidates that the chimeric poliovirus PVS-3m/p24 of the present invention is able to express integrated HIV-1 p24 protein effectively.

Example 6

Maintenance of Antigenicity of Exogenous Vaccine Protein Expressed by the Chimeric Poliovirus PVS-3m/p24

In order to determine whether the HIV-1 p24 protein produced by chimeric poliovirus PVS-3m/p24 in Example 4 is able to retain the antigenicity of wild type p24, radioimmunoprecipitation assay was performed with anti-p24 antibody.

Chimeric poliovirus PVS-3m/p24 was inoculated into HeLa cell at moi of 10. Five hours after infection, cells were transferred to a fresh DMEM without methionine/cystein (GIBCO/BRL). After starvation for 1 hr, isotope-labeled methionie/cystein [($L-^{35}S$)-Met/Cys, specific activity >1000 Ci/mmole; Amersham] was added to the medium at a final concentration of 50 µCi/mmole, and then cultured for additional 2 hrs. Cells were harvested by trypsinization, washed twice with PBS, and then lysed with 500 µl of radioimmunoprecipitation assay (RIPA) buffer (150 mM NaCl, 1% of NP-40, 0.5% of DOC, 0.1% of SDS, 50 mM Tris-Cl pH 8.0) on ice for 10 minutes. After centrifugation to remove nucleus and cell debris. 3 µl of rabbit anti-p24 antiserum was added to the supernatant and the mixture was allowed to react at 4° C. for 12 hours. 80 µl of 10% protein A-sepharose in PBS was added to the reaction mixture and allowed to react with antibody at room temperature for 1 hour, followed by centrifugation to recover sepharose beads. The antigen-bead complex was washed three times with RIPA buffer, resuspended with 50 μl of 1× sample buffer, boiled for 3 minutes, separated on 10% SDS-PAGE, and then followed by autoradiogram to detect antibody-reactive antigens in the lysate of infected cells. The results are shown in FIG. 7.

The results shown in FIG. 7 clearly demonstrate that the HIV-1 p24 protein produced by chimeric poliovirus PVS-3m/p24 of the present invention has the similar antigenicity to that of wild type p24 of HIV-1.

Example 7

Genetic Stability of Chimeric Poliovirus PVS-3m/p24

In order to evaluate th6e genetic stability of chimeric poliovirus PVS-3m/p24 of Example 4, the chimeric progeny virus of PVS-3m/p24 was consecutively passaged in HeLa cells and the integrity of the cloned gene was determined by performing RT-PCR from the viral RNA extracted from each passage of virus. Viral particles were precipitated by adding PEG/NaCl at a final concentration of 5%/0.125M, respectively. Standing for 30 minutes at room temperature, the mixture was precipitated by centrifugation for 10 minutes. Viral RNA was obtained by phenol-chloroform extraction and ethanol precipitation.

The extracted RNA (10 μg) was mixed with cDNA synthesis primer (SEQ. ID. NO. 13) (1 μg), and the mixture was subjected to denaturation at 70° C. for 10 minutes. The mixture was quickly transferred on ice, and then reverse transcriptase reaction solution (50 mM Tris-HCl: pH 8.3, 65 mM KCl, 3 mM $MgCl_2$, 10 mM DTT, 1 mM DNTP mixture, 20 units of RNAsin) and 200 units of reverse transcriptase of MMLV (Moloney Murine Leukemia virus; GIBCO/BRL) were added thereto, followed by reaction at 42° C. for 60 minutes. The reaction mixture was incubated at 100° C. for 3 minutes to inactivate enzymes.

RT-PCR was conducted to amplify the manipulated region containing the cloned exogenous gene by using Sabin type 1 sense primer (SEQ. ID. NO. 14) and Sabin type 1 antisense primer (SEQ. ID. NO. 15). The RT-PCR was performed with Taq polymerase (Bioneer, Korea) for 25 cycles at 94° C. for 1 minute, 45° C. for 30 seconds, and 72° C. for 45 seconds for each cycle. The results are shown in FIG. 8.

Figure 8:
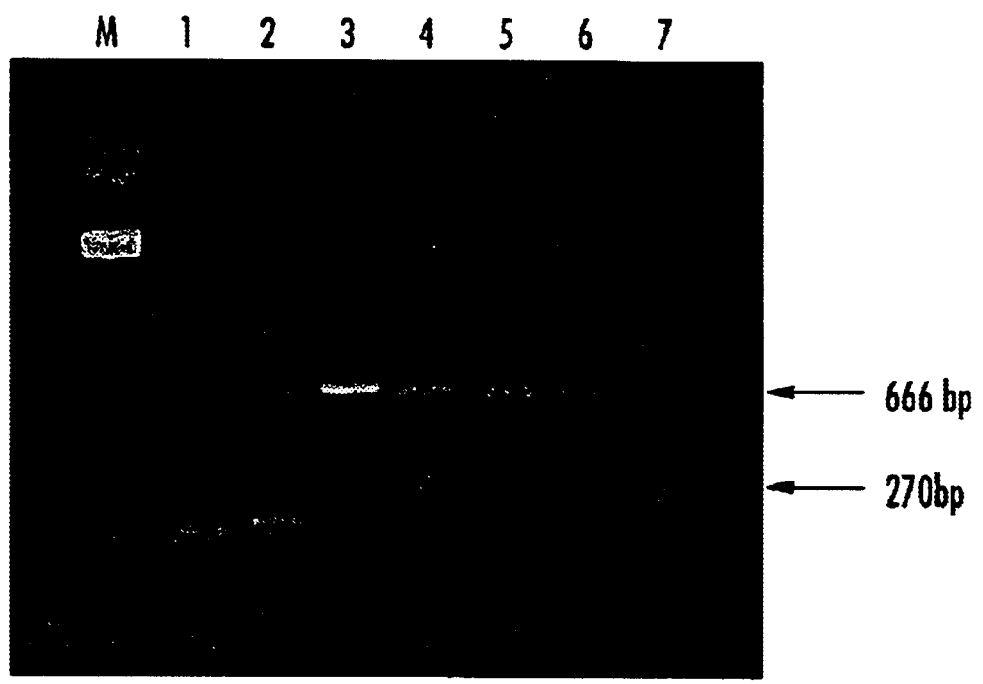
FIG. 8 represents the PCR analysis of p24 gene, cloned in chimeric poliovirus, up to 12th passage to evaluate the genetic stability of chimeric poliovirus PVS-3m/p24 during the passages:
  Lane 1: PCR product from wild Sabin type 1 poliovirus-infected HeLa cell
  Lane 2: PCR product from recombinant poliovirus PVS-3m-infected HeLa cell
  Lane 3: PCR product from chimeric poliovirus PVS-3m/p24-infected HeLa cell
  Lane 4: PCR product from the second(2nd)-passaged chimeric poliovirus PVS-3m/p24-infected HeLa cell
  Lane 5: PCR product from the fourth(4th)-passaged chimeric poliovirus PVS-3m/p24-infected HeLa cell
  Lane 6: PCR product from the eighth(8th)-passaged chimeric poliovirus PVS-3m/p24-infected HeLa cell
  Lane 7: PCR product from the twelveth(12th)-passaged chimeric poliovirus PVS-3m/p24-infected HeLa cell
Figure 9:
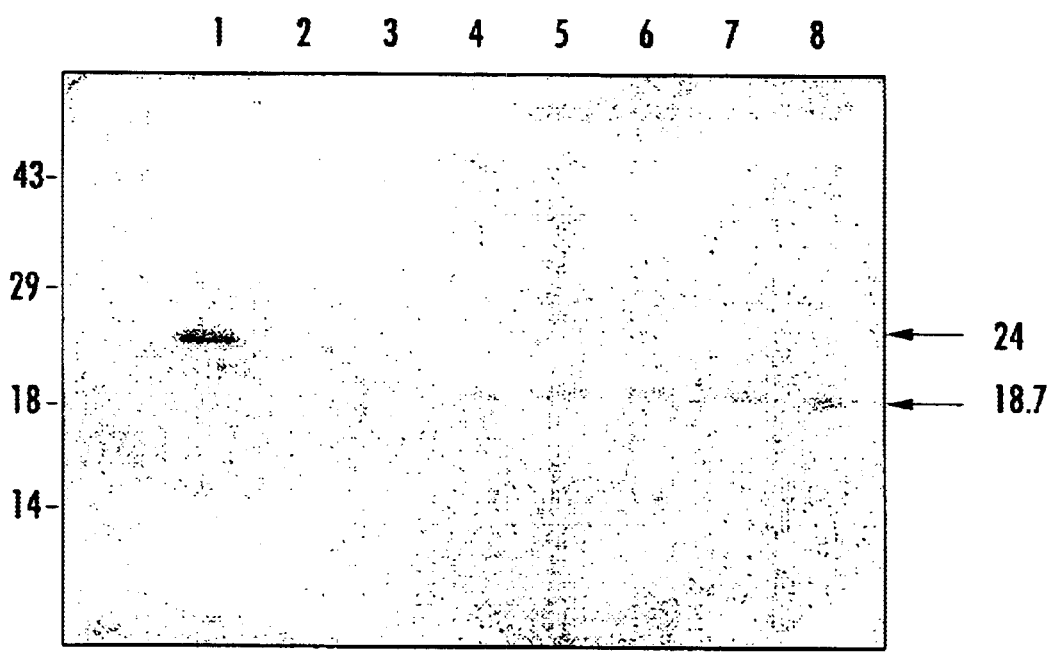
FIG. 9 is the results of western blot of HIV-1 p24 protein, expressed from the chimeric poliovirus, up to 12th passage to evaluate the expression stability of chimeric poliovirus PVS-3m/p24 during the passages:
  Lane 1: HIV-1/-tat
  Lane 2: HeLa cell lysate
  Lane 3: Wild-type Sabin 1 poliovirus-infected HeLa cell lysate
  Lane 4: Cell lysate of first(1st)-passaged chimeric poliovirus PVS-3m/p24-infected HeLa cell
  Lane 5: Cell lysate of third(3rd)-passaged chimeric poliovirus PVS-3m/p24-infected HeLa cell
  Lane 6: Cell lysate of sixth(6th)-passaged chimeric poliovirus PVS-3m/p24-infected HeLa cell
  Lane 7: Cell lysate of ninth(9th)-passaged chimeric poliovirus PVS-3m/p24-25 infected HeLa cell
  Lane 8: Cell lysate of twelveth(12th)passaged chimeric poliovirus PVS-3m/p24-infected HeLa cell

In FIG. 8, the band shown at 666 bp consists of the cloned p24 gene (504 bp, 169aa) and parts of the poliovirus genome around the cloning site. Whereas the band at 270 bp suggests there are some internal deletions in the cloned p24 gene during the steps of transfection and passages of recombinant chimeric virus. Nevertheless, the result that the band intensity at 666 bp was not weakened as passage goes on as shown in FIG. 8, strongly suggests that the chimeric poliovirus PVS-3m/p24 of the present invention is very stable to carry the cloned exogenous gene over 12th passage. The genetic stability of the chimeric virus was also confirmed by analysis of the p24 expression patterns of the chimeric virus during the passages.

The expression pattern of HIV-1 p24 protein during the passages of chimeric virus was observed. HeLa cells were inoculated with chimeric progeny virus of each passage at 10 moi. Cells were harvested 8 hours p.i., and the lysates were subjected to electrophoresis on SDS-PAGE, followed by Western blot hybridization with rabbit anti-p24 antiserum. The results are shown in FIG. 9.

The results shown in FIG. 9 make it affirm that the chimeric poliovirus PVS-3m/p24 is very stable to express cloned p24 protein constantly over 12th passage, indicating that the integrated exogenous gene is efficiently preserved during the passages.

These experimental results substantiate that chimeric poliovirus PVS-3m/p24 of the present invention, obtained by introducing HIV-1 p24 gene (169aa) into the multiple cloning site of recombinant vector pTZ-PVS-3m, can efficiently express cloned p24 protein, which has the similar antigenicity to that of the wild type HIV-1 p24 protein. Moreover, chimeric poliovirus PVS-3m/p24 conserves the sequence of the cloned p24 gene as well as keeps good expression level of p24 protein over 12 passages, indicating that the chimeric poliovirus PVS-3m/p24 is genetically stable enough to be used as a clone.

Considering that Sabin type 1 strain of poliovirus, which is used as a starting vector for the present invention, has never been reported to cause any adverse side effect to human being up to now, the chimeric poliovirus PVS-3m/p24 of the present invention is highly expected to be used as a powerful CTL-inducible mucosal vaccine candidate against AIDS, as suggested by Walker and his colleagues (Science 280, 825, 1998, Rosenberg eat al., Science, 278, 1447, 1997).

For the present invention, the possibility whether the recombinant plasmid pTZ-PVS-3m could be used as a useful vaccine vector to express HIV-1 envelope glycoprotein gp120, especially V3 region, was evaluated. Thus, the gene coding for 125 amino acid residues covering V3 loop region of HIV-1 gp 120 was introduced into the multiple cloning site of the recombinant plasmid pTZ-PVS-3m, followed by production of chimeric poliovirus PVS-3m/env. The expression of cloned exogenous env gene and genetic stability of chimeric poliovirus PVS-3m/env were evaluated.

Example 8

Construction of Recombinant Poliovirus Plasmid pTZ-PVS-3m/env and Production of Chimeric Poliovirus PVS-3m/env A cDNA fragment (375 bp) coding for 125 amino acid residues (amino acid sequence of env protein at 251–375) including V3 loop region of HIV-1 gp 120 was amplified by PCR and introduced into the multiple cloning site of recombinant vector pTZ-PVS-3m, as described in FIG. 10.

Two primers: SstII-env-sense primer (SEQ. ID. NO. 15) and EagI-env-antisense primer (SEQ. ID. NO. 165 having restriction enzyme SstII and EagI-recognition sites at 5'-end and 3'-end, respectively, were employed to amplify the designed region of env(125aa) gene from the HXB2 (obtained from NIH AIDS Research and Reference Reagent Program, US.) by PCR.

PCR product was digested with SstII and EagI, and the gene fragment of 375 bp was introduced into the corresponding SstII and EagI sites of the vector pTZ-PVS-3m of Example 1 to produce recombinant plasmid pTZ-PVS-3m/env (FIG. 10).

By following the procedures in Example 2, plasmid pTZ-PVS-3m/p24 was in vitro transcribed, and the RNA transcripts were transfected into HeLa cells monolayered in 60 mm culture plate. The transfected HeLa cells were cultivated in DMEM medium supplemented with 10% FCS at 37° C. $CO_2$ incubator for 2 days. When full CPE was observed, the culture supernatants were harvested and used as a source of chimeric poliovirus PVS-3m/env.

Example 9

One-step Growth Curve for the Chimeric Poliovirus PVS-3m/env

In order to evaluate the replication capacity of the chimeric poliovirus expressing HIV-1 env protein, one-step growth curve was determined by measuring the virus titer of culture supernatants at each time point following the procedures described in Example 4. The experiments were repeated four times and the averages are shown in Table 2.

These experimental results substantiate that chimeric poliovirus PVS-3m/env of the present invention, obtained by introducing HIV-1 env gene (125aa) into the multiple cloning site of recombinant vector pTZ-PVS-3m, can efficiently express cloned env gene. Moreover, chimeric poliovirus PVS-3m/env conserves the intact sequence of the cloned env gene as well as keeps good expression level of env protein over 12 passages, indicating that the chimeric poliovirus PVS-3m/env is genetically stable enough to be used as a clone for vaccine candidate,

TABLE 2

| | Virus Titer ($TCID_{50}$/ml) after infection | | | | | | | |
|---|---|---|---|---|---|---|---|---|
| | 0 hour | 3 hours | 6 hours | 9 hours | 12 hours | 15 hours | 18 hours | 21 hours |
| PVS | 0 | 0 | $2.6 \times 10^4$ | $4.1 \times 10^5$ | $4.1 \times 10^5$ | $1.6 \times 10^6$ | $6.6 \times 10^6$ | $6.6 \times 10^6$ |
| PVS-3m | 0 | 0 | $1.6 \times 10^3$ | $6.4 \times 10^3$ | $2.6 \times 10^4$ | $2.1 \times 10^5$ | $1.6 \times 10^6$ | $1.6 \times 10^6$ |
| PVS-3m/env | 0 | 0 | $4.0 \times 10^2$ | $1.6 \times 10^3$ | $6.4 \times 10^3$ | $2.6 \times 10^4$ | $1.0 \times 10^5$ | $1.0 \times 10^5$ |

As shown at Table 2, the replication capacity of the chimeric poliovirus PVS-3m/env was maximum 1 log lower than that of wild type Sabin 1(PVS), but was similar to that of PVS-3m.

Example 10

Expression Pattern of Exogenous env Protein During the Replication of Chimeric Poliovirus PVS-3m/env It was determined whether the chimeric poliovirus PVS-3m/env expresses the cloned env protein during its growth. Chimeric poliovirus PVS-3m/env was inoculated into HeLa cells at 10 moi. Eight hours p.i., infected cells were harvested and subjected to electrophoresis on 10% SDS-PAGE. Then, Western blot hybridization was conducted with AIDS patients' sera, and the results are shown in FIG. 11. The results shown in FIG. 11 make it affirm that chimeric poliovirus PVS-3m/env of the present invention effectively expresses HIV-1 env protein (125aa, 15 kDa).

Example 11

Genetic Stability of Chimeric Poliovirus PVS-3m/env

In order to evaluate the genetic stability of chimeric poliovirus PVS-3m/env of Example 8, the chimeric progeny virus of PVS-3m/env was consecutively passaged in HeLa cells and the integrity of the cloned gene (375 bp) was determined by conducting RT-PCR following the same procedure as described in Example 7. The results are shown in FIG. 11. The results shown in FIG. 11 elucidate that the chimeric poliovirus PVS-3m/env of the present invention is very stable to carry the exogenous gene over 12th passage.

Moreover, the genetic stability of the chimeric poliovirus was also confirmed by analysis of the env expression patterns of the chimeric virus during the passages.

The expression pattern of HIV-1 env protein during the passages of chimeric virus was determined by the same procedure as described in Example 7 except using AIDS patients' sera for western blot hybridization. The results are shown in FIG. 12. The results in FIG. 12 make it affirm that the chimeric poliovirus PVS-3m/env expresses cloned env protein (125aa) constantly over 12th passage, indicating that the cloned exogenous gene is efficiently preserved during the passages.

Considering that the Sabin type 1 strain of poliovirus, which is used as a starting vector for the present invention, has never been reported to raise any adverse side effect to human being up to now, the chimeric poliovirus PVS-3n/env of the present invention is highly expected to be used as a powerful oral mucosal vaccine against AIDS.

As denoted above, the recombinant vector pTZ-PVS-3m of the present invention has a multiple cloning site and 3C-protease cleavage site so as to make it easy to introduce various exogenous vaccine gene into the recombinant Sabin 1 poliovirus, and facilitate to produce genetically stable chimeric polioviruses which can be used as oral vaccines against several infectious viral disease by taking advantages of the Sabin 1 poliovirus.

For the present invention, in order to evaluate the possibility that the recombinant vector pTZ-PVS-3m can be applicable as a useful vaccine vector to other infectious viral diseases than AIDS, the core protein-coding gene of Hepatitis C virus (HCVc) was cloned into the recombinant vector pTZ-PVS-3m. Thus, a part of core gene coding for 100 amino acid residues of N-terminal was introduced into the multiple cloning site of recombinant vector pTZ-PVS-3m, followed by production of chimeric poliovirus PVS-3m/HCVc. The expression of cloned exogenous HCVc gene and genetic stability of the chimeric poliovirus PVS-3m/HCVc were evaluated.

Example 12

Construction of Chimeric Poliovirus Plasmid pTZ-PVS-3m/HCVc and Production of Chimeric Poliovirus PVS-3m/HCVc HCVc gene coding for 100 amino acid residues of N-terminal core was amplified by PCR and introduced into the multiple cloning site of recombinant poliovirus pTZ-PVS-3m, as described in FIG. 13.

Two primers: SstII-HCVc-sense primer (SEQ. ID. NO. 17) and EagI-HCVc-antisense primer (SEQ. ID. NO. 18) were employed to amplify the designed region of HCV core gene (300 bp, 100aa) from the template of pcDNA/Neo-HCVcore plasmid (obtained by courtesy from Dr. Sung at Postech, Korea) by PCR.

PCR product was digested with SstII and EagI, and the gene fragment of 300 bp was introduced into the corresponding SstII and EagI sites of the plasmid pTZ-PVS-3m of Example 11 to produce recombinant plasmid pTZ-PVS-3m/HCVc (FIG. 13).

By following the procedure in Example 2, plasmid pTZ-PVS-3m/HCVc was in vitro transcribed, and the RNA transcripts were transfected into the HeLa cells monolayered in 60 mm culture plate. The transformed HeLa cells were cultivated in DMEM medium supplemented with 10% FCS at 37° C. $CO_2$ incubator for 2 days. When full CPE was observed, the culture supernatants were harvested and used as a source of chimeric poliovirus PVS-3m/HCVc.

37° C., 25 $\mu$Ci/ml of [5,6$^3$H]-uridine (Amersham; specific activty 45 Ci/mmole) was added. The cells were harvested every 3 hrs, washed 3 times with PBS, and then lysed by adding 0.5 ml of lysis buffer (80 mM NaCl, 5 mM $MgCl_2$, 10 mM Tris-Cl 8.2, 1 mM DTT, 10 mM vanadyl ribonuclease complex, and 0.5% of NP-40) for 5 min on ice. Trichloroacetic acid was added to the lysates to a final concentration of 20%, and the lysates were incubated on ice for 30 min. The samples were filtrated with glass fiber filters (Whatsman, GF-C filter), and the radioactivty was determined by scintillation counter (Hewlett Packard) and the results are shown in Table 4.

TABLE 4

|  | [$^3$H]-uridine (cpm) in viral RNA | | | | | | |
|---|---|---|---|---|---|---|---|
|  | 0 hour | 3 hours | 6 hours | 9 hours | 12 hours | 15 hours | 18 hours |
| PVS | 0 | $1.1 \times 10^4$ | $4.0 \times 10^5$ | $1.6 \times 10^5$ | $1.4 \times 10^5$ | $1.1 \times 10^5$ | $4.8 \times 10^4$ |
| PVS-3m | 0 | $1.2 \times 10^4$ | $3.9 \times 10^5$ | $1.6 \times 10^5$ | $1.4 \times 10^5$ | $1.0 \times 10^5$ | $5.0 \times 10^4$ |
| PVS-3m/HCVc | 0 | $1.2 \times 10^5$ | $3.7 \times 10^5$ | $1.6 \times 10^5$ | $1.3 \times 10^5$ | $1.0 \times 10^7$ | $4.8 \times 10^4$ |

Example 13

One-step Growth Curve for the Chimeric Poliovirus PVS-3m/HCVc

In order to evaluate the replication capacity of the chimeric poliovirus expressing HCV core protein, one-step, growth curve was determined by measuring the virus titer of culture supernatants at each time point following the procedures described in Example 4. The results are shown at Table 3 and FIG. 14. The values in Table 3 are averages from four repeat experiments.

As shown at Table 4, the kinetics of RNA synthesis of the chimeric poliovirus PVS-3m/HCVc is almost similar to the pattern of wild-type (PVS) or recombinant poliovirus PVS-3m in the infected HeLa cells except the level at 6 hours after the infection. The results suggest that the lower replication capacity (about 5 times lower) of the chimeric virus in Example 13 is not to be due to reduced RNA synthesis, but seems to be, due to the unefficient protein processing of the chimeric virus at assembly steps.

In conclusion, considering the fact that chimeric poliovirus PVS-3m/HCVc has the similar capacity of RNA synthesis to those of wild-type or recombinant virus, the reduced replication capacity (about 5 times lower than that

TABLE 3

|  | Virus Titer (TCID$_{50}$/ml) after infection | | | | | | | |
|---|---|---|---|---|---|---|---|---|
|  | 0 hour | 3 hours | 6 hours | 9 hours | 12 hours | 15 hours | 18 hours | 21 hours |
| PVS | 0 | 0 | $5.0 \times 10^5$ | $2.5 \times 10^6$ | $7.5 \times 10^7$ | $4.0 \times 10^7$ | $7.5 \times 10^7$ | $1.0 \times 10^8$ |
| PVS-3m | 0 | 0 | $2.5 \times 10^5$ | $2.0 \times 10^6$ | $5.0 \times 10^7$ | $5.0 \times 10^7$ | $2.5 \times 10^7$ | $7.5 \times 10^7$ |
| PVs-3m/HCVc | 0 | 0 | $1.0 \times 10^5$ | $5.0 \times 10^6$ | $7.5 \times 10^6$ | $1.0 \times 10^7$ | $2.0 \times 10^7$ | $5.0 \times 10^7$ |

As shown in Table 3 and FIG. 14, the chimeric poliovirus PVS-3m/HCVc shows replication capacity of at the most 10 times lower than of that of the wild-type (PVS) at 12 hours p.i. The average replication capacity of the chimeric poliovirus PVS-3m/HCVc is about 5 times lower than that of the wild-type Sabin 1 and 3 times lower than that of the recombinant poliovirus PVS-3m.

Example 14

RNA Synthesis of Chimeric Poliovirus PVS-3m/HCVc

Following the previous report (Mattion et al., J. Virol. 68, 3925, 1994) the experiment was performed. HeLa cells grown in 24-well plates were mock infected or infected with 10 moi of wild type and chimeric poliovirus PVS-3m/HCVc. After adsorption for 1 hr at room temperature the cells were washed with PBS and fed in DMEM containing Actinomicin D (5 $\mu$g/ml, Difco). After incubation for 1 hr at of wild type PVS) of the chimeric poliovirus PVS-3m/p24 may not adversely affect for using the chimeric poliovirus as oral vaccine:

Example 15

Expression Pattern of Exogenous HCVc Protein During the Replication of Chimeric Poliovirus PVS-3m/HCVc In order to determine whether the chimeric poliovirus PVS-3m/HCVc expresses HCV core protein during its growth. Chimeric poliovirus PVS-3m/HCVc was inoculated into monolayered HeLa cells at 10 moi for 1 hour, and the unadsorbed viruses were removed. The infected cells were further cultivated at 37° C. $CO_2$ incubator. The cells were harvested 8 hrs p.i, and subjected to electrophoresis on 10% SDS-PAGE. Western blot hybridization was cperformed with a rabbit antiserum (obtained by courtesy of Dr. Hwang at Hallim University, Korea) or monoclonal antibody against HCV core protein (Bio-genesis, Sandown, N.H., USA), and the results are shown in FIG. 15. The western blot signal shown in FIG. 15 (Lane 3) elucidated that chimeric poliovirus PVS-3m/HCVc of the present invention effectively expresses cloned HCV core protein (100aa, 12 kDa).

In FIG. 15, several bands other than the one at the desired 12 kDa are assumed to be due to HCV core protein fused to the hydrophobic cell organells by the hydrophobic residues at the N-terminal end of the HCV core protein. To confirm this hypothesis, recombinant viural pellet (lane 4), virus-free culture supernatant concentrate (lane 5), or precipitant of the cell lysate (lane 6) or supernatant of the cell lysate (lane 7) of chimeric poliovirus PVS-3m/HCVc-infected HeLa cells were analyzed by western blot hybridization using the same antiserum. The precipitate (lane 6) and supernatant (lane 7) of the cell lysates were obtained by treating the infected cells with 1% NP-40. As shown in FIG. 15, only the precipitant (lane 6) and supernatant (lane 7) of the infected HeLa cell lysates show the signal of antigen bands when screened with the specific antiserum, suggesting that the signals are not to be due to the non-specific reaction of antiserum. Moreover, the fact that the precipitant fraction (lane 6) shows a more clear and intensive band at 12 kDa makes the assumption much more convincing. These results are in part consistent with the previous report that the assembly of HCV occurs in lumen of endoplasmic reticulum, but not in cytoplasm, and forms a membrane-bound vesicles (Dubission et al., 1994). If the HCV core protein-cell organell complex does not affect the replication of the recombinant virus, the complex will be much more effective to induce CTL immunity together with humoral impunity against HCV.

Example 16

Genetic Stability of Chimeric Poliovirus PVS-3m/HCVc

In order to evaluate the genetic stability of chimeric poliovirus PVS-3m/HCVc of Example 12, the progeny virus of PVS-3m/HCVc is consecutively passaged in HeLa cells and the integrity of the cloned gene (300 bp) was determined by conducting RT-PCR following the same procedure as described in Example 7.

The results are shown in FIG. 16, in which a strong band at 459 bp was clearly appeared at each sample regardless the number of passages. No other band due to the internal deletion as shown in the PVS-3m/p24, or insertion was detected during the passages.

Thus, the results in FIG. 16 elucidate that the chimeric poliovirus PVS-3m/HCV of the present invention is very stable to carry the exogenous gene over 12th passage.

Moreover, the genetic stability of the chimeric poliovirus was also confirmed by analysis of the HCVc expression patterns of the chimeric virus during the passages The expression pattern of HCV core protein during the passages of recombinant virus was determined by the same procedure as described in Example 7 except using monoclonal antibody against HCV core protein (Bio-genesis, Sandown, N.H., USA) for Western blot hybridization. The results are shown in FIG. 17. Results shown in FIG. 17 make it affirm that the chimeric poliovirus PVS-3m/HCVc expresses HCV core protein (100aa) constantly over 12th passage.

These experimental results substantiate that chimeric poliovirus PVS-3m/HCVc of the present invention, obtained by introducing HCV core gene (100aa) into the multiple cloning site of recombinant vector pTZ-PVS-3m, can efficiently expresses cloned HCV core gene. Moreover, it conserves the intact sequence of cloned HCV core gene and keeps good expression level of the HCV core protein over 12 passages, indicating that the chimeric poliovirus PVS-3m/HCVc is genetically stable enough to be used as a clone for HCV vaccine candidate.

Considering that the Sabin type 1 strain of poliovirus, which is used as a starting vector for the present invention, has never been reported to raise any adverse side effect to human being up to now, the chimeric poliovirus PVS-3m/HCVc of the present invention is highly expected to be used as a powerful oral mucosal vaccine against HCV.

As shown above, the recombinant vector pTZ-PVS-3m of the present invention has a multiple cloning site and 3C-protease cleavage site so as to make it easy to introduce various exogenous vaccine gene into the recombinant Sabin 1 poliovirus, ⌣d facilitate to produce genetically stable chimeric polioviruses which can be used as oral vaccines against several infectious viral disease by taking advantages of the Sabin 1 poliovirus.

Although preferred embodiments of the present invention have been described in detail herein above, it should be clearly understood that many variations and/or modifications of the basic inventive concepts herein taught which may appear to those skilled in the art will still fall within the spirit and scope of the present invention as defined in the appended claims.

What is claimed is:

1. A replication-competent, genetically stable, recombinant Sabin type I poliovirus vector which comprises:
   (a) nucleotides 1–745 of SEQ ID NO: 1, wherein positions 743–745 are ATG;
   (b) a multiple cloning site directly linked 3' to said ATG;
   (c) a 3C-protease cleavage site coding for the amino acid sequence of Ala-Leu-Phe-Gln (SEQ ID NO: 30) which is directly linked 3' to said multiple cloning site; and
   (d) nucleotides 746 to 7440 of SEQ ID NO: 1.

2. The vector according to claim 1, wherein said sequence coding for the multiple cloning site and 3C-protease cleavage site consists of a nucleotide sequence of SEQ ID NO:20.

3. The vector according to claim 1 wherein the vector is pTZ-PVS-3m (KCTC-0365BP).

4. A replication-competent, genetically stable, recombinant chimeric Sabin type 1 poliovirus vector wherein the exogenous nucleotide sequence is stably maintained in the vector for at least 12 passages comprising:
   (a) nucleotides 1–745 of SEQ ID NO: 1, wherein positions 743–745 are ATG;
   (b) a nucleotide sequence comprising a multiple cloning site directly linked 3' to said ATG and which further comprises an exogenous nucleotide sequence encoding an exogenous polypeptide to be expressed;
   (c) a 3C-protease cleavage site coding for the amino acid sequence of Ala-Leu-Phe-Gln (SEQ ID NO: 30) which is directly linked 3' to said nucleotide sequence comprising a multiple cloning site and an exogenous nucleotide sequence; and
   (d) nucleotides 746 to 7440 of SEQ ID NO: 1.

5. The vector according to claim 4, wherein said exogenous polypeptide is derived from an infectious virus.

6. The vector according to claim 4 wherein said exogenous nucleotide sequence encodes the envelope glycoprotein of the V3 loop of the HIV-1 gp-120.

7. A host cell transfected with a replication-competent recombinant Sabin Type I poliovirus vector of claim 1.

8. A host cell transfected with a replication-competent chimeric Sabin type I poliovirus vector of claim 4.

9. A host cell according to claim 8 wherein said exogenous nucleotide sequence encodes the V3 loop of HIV-1 gp120 glycoprotein.

10. A method for producing a replication-competent, genetically stable, chimeric Sabin type 1 poliovirus vector which expresses an exogenous polypeptide as a component of a recombinant polyprotein precursor that is proteolytically processed with the result that said exogenous polypeptide is released from said polyprotein precursor, the method comprising the steps of:
   a) providing a replication-competent Sabin type 1 poliovirus;
   b) introducing a multiple cloning site directly after the first initiation codon (ATG) of said polyprotein precursor;
   c) introducing a 3C-protease cleavage site coding for the amino acid sequence of Ala-Leu-Phe-Gln (SEQ ID NO: 30) which is directly linked 3' to said multiple cloning site,
   d) introducing an exogenous nucleotide sequence encoding said exogenous polypeptide to be expressed in the multiple cloning site; and,
   e) isolating the recombinant vector.

11. The vector according to claim 4, wherein said multiple cloning site comprises a SstII (CCGCGC) and a EagI (CGGCCG) restriction site.

12. A method according to claim 10 wherein said multiple cloning site and said 3C-protease cleavage site consists essentially of a nucleotide sequence of SEQ ID NO:20.

13. A method according to claim 10 wherein said exogenous nucleotide sequence encodes a envelope glycoprotein of the V3 loop of the HIV-1 gp-120.

* * * * *

SEQUENCE LISTING

```
<160> NUMBER OF SEQ ID NOS: 30

<210> SEQ ID NO 1
<211> LENGTH: 7441
<212> TYPE: DNA
<213> ORGANISM: Human poliovirus 1

<400> SEQUENCE: 1
ttaaaacagc tctggggttg cacccgcccc agaggcccac gtggcggcta gtactccggt      60
attgcggtac ccttgtacgc ctgttttata ctcccttccc gtaacttaga cgcacaaaac     120
caagttcaat agaaggggt acaaaccagt accaccacga acaagcactt ctgtttcccc     180
```

-continued

```
ggtgatgttg tatagactgc ttgcgtggtt gaaagcgacg gatccgttat ccgcttatgt      240
acttcgagaa gcccagtacc acctcggaat cttcgatgcg ttgcgctcag cactcaaccc      300
cagagtgtag cttaggctga tgagtctgga catccctcac cggtgacggt ggtctaggct      360
gcgttggcgg cctacctatg gctaacgcca tgggacgcta gttgtgaaca aggtgtgaag      420
agcctattga gctacataag aatcctccgg cccctgaatg cggctaatcc caacctcggg      480
gcaggtggtc acaaaccagt gattggcctg tcgtaacgcg caagtccgtg gcggaaccga      540
ctactttggg tgtccgtgtt tccttttatt ttattgtggc tgcttatggt gacaatcaca      600
gattgttatc ataaagcgaa ttggattggc catccggtga agtgagatt cattatctat       660 ctgtttgctg gattcgctcc attgagtgtg tttactctaa gtacaatttc aacagttatt      720
tcaatcagac aattgtatca taatgggtgc tcaggtttca tcacagaaag tgggcgcaca      780
tgaaaactca aatagagcgt atggtggttc taccattaat tacaccacca ttaattatta      840
tagagattca gctagtaacg cggcttcgaa acaggacttc tctcaagacc cttccaagtt      900
caccgagccc atcaaggatg tcctgataaa aacatcccca atgctaaact cgccaaacat      960
agaggcttgc gggtatagcg atagagtact gcaattaaca ctgggaaact ccactataac     1020
cacacaggag gcggctaatt cagtagtcgc ttatgggcgt tggcctgaat atctgaggga     1080
cagcgaagcc aatccagtgg accagccgac agaaccagac gtcgctgcat gcaggtttta     1140
tacgctagac accgtgtctt ggacgaaaga gtcgcgaggg tggtggtgga agttgcctga     1200
tgcactgcgg gacatgggac tctttggcca aaatatgtac taccactacc taggtaggtc     1260
cgggtacacc gtgcatgtac agtgtaacgc ctccaaattc caccagggg cactaggggt      1320 attcgccgta ccagagatgt gtctggccgg ggatagcaac accactacca tgcacaccag     1380
ctatcaaaat gccaatcctg gcgagaaagg aggcactttc acgggtacgt tcactcctga     1440
cgacaaccag acatcacctg cccgtaggtt ctgcccggtg gattacctct ttggaaatgg     1500
cacgttattg gggaatgcct ttgtgttccc gcaccagata ataaacctac ggaccaacaa     1560
ctgtgctaca ctggtactcc cttacgtgaa ctccctctcg atagatagta tggtaaagca     1620
caataattgg ggaattgcaa tattaccatt ggccccatta aattttgcta gtgagtcctc     1680
cccagagatt ccaatcacct tgaccatagc ccctatgtgc tgtgagttca atggattaag     1740
aaacattacc ctgccacgct tacagggcct gccggtcatg aacacccctg gtagcaatca     1800
atatcttact gcagacaact tccagtcacc gtgtgcgctg cctgaatttg atgtgacccc     1860
acctattgac atacccggtg aagttaagaa catgatggaa ttggcagaaa tcgacaccat     1920
gattcccttt gacttaagtg caaaaaaaaa gaacaccatg gaaatgtata gggttcggtt     1980
aagtgacaaa ccacatacag acgatcccat actctgcctg tcactctctc cagcttcaga     2040
tcctaggttg tcatatacta tgcttggaga atcctaaat tactacacac actgggcagg      2100
atccctgaag ttcacgtttc tgttctgtgg atccatgatg gcaactggca aactgttggt     2160
gtcatacgcg cctcctggag ccgacccacc aaagaagcgt aaggaggcga tgttgggaac     2220
acatgtgatc tgggacatag gactgcagtc ctcatgtact atggtagtgc catggattag     2280
caacaccacg tatcggcaaa ccatagatga tagtttcacc gaaggcggat acatcagcgt     2340
cttctaccaa accagaatag tcgtccctct ttcgacaccc agagagatgg acatccttgg     2400
ttttgtgtca gcgtgtaatg acttcagcgt gcgcttgatg cgagataca cacatataga      2460 gcaaaaagcg ctagcacagg ggttaggtca gatgcttgaa agcatgattg acaacacagt     2520
ccgtgaaacg gtgggggcgg caacgtctag agacgctctc ccaaacactg aagccagtgg     2580
```

```
accagcacac tccaaggaaa ttccggcact caccgcagtg gaaactgggg ccacaaatcc      2640
actagtccct tctgatacag tgcaaaccag acatgttgta caacataggt caaggtcaga      2700
gtctagcata gagtctttct tcgcgcgggg tgcatgcgtg gccattataa ccgtggataa      2760
ctcagcttcc accaagaata aggataagct atttacagtg tggaagatca cttataaaga      2820
tactgtccag ttacggagga aattggagtt cttcacctat tctagatttg atatggaatt      2880
tacctttgtg gttactgcaa atttcactga gactaacaat gggcatgcct taaatcaagt      2940
gtaccaaatt atgtacgtac caccaggcgc tccagtgccc gagaaatggg acgactacac      3000
atggcaaacc tcatcaaatc catcaatctt ttacacctac ggaacagctc cagcccggat      3060
ctcggtaccg tatgttggta tttcgaacgc ctattcacac ttttacgacg ttttttccaa      3120
agtaccactg aaggaccagt cggcagcact aggtgactcc ctctatggtg cagcatctct      3180
aaatgacttc ggtattttgg ctgttagagt agtcaatgat cacaacccga ccaaggtcac      3240
ctccaaaatc agagtgtatc taaaacccaa acacatcaga gtctggtgcc cgcgtccacc      3300
gagggcagtg gcgtactacg gccctggagt ggattacaag gatggtacgc ttacacccct      3360
ctccaccaag gatctgacca catatggatt cggacaccaa acaaagcgg tgtacactgc      3420 aggttacaaa atttgcaact accatttggc cactcaggaa gatttgcaaa acgcagtgaa      3480
cgtcatgtgg aatagagacc tcttagtcac agaatcaaga gcccagggca ccgattcaat      3540
cgcaaggtgc aattgcaacg caggggtgta ctactgcgag tctagaagga atactaccc      3600 agtatccttc gttggcccaa cgttccagta catggaggct aataactatt acccagctag      3660
gtaccagtcc catatgctca ttggccatgg attcgcatct ccaggggatt gtggtggcat      3720
actcagatgt caccacgggg tgatagggat cattactgct ggtggagaag ggttggttgc      3780
atttacagac attagagact tgtatgccta cgaagaagaa gccatggaac aaggcatcac      3840
caattacata gagtcacttg gggccgcatt tggaagtgga tttactcagc agattggaga      3900
caaaataaca gagttgacta atatggtgac cagtaccatc actgaaaagc tacttaagaa      3960
cttgatcaag atcatatcct cactagttat tataaactagg aattatgaag acaccacaac      4020
agtgctcgct accctggccc ttcttgggtg tgatgcttca ccatggcagt ggcttagaaa      4080
gaaagcatgc gatgttctgg agataccta tgtcaccaag caaggtgaca gttggttgaa      4140
gaagtttact gaagcatgca acgcagctaa gggactggag tgggtgtcaa acaaaatctc      4200
aaaattcatt gattggctca aggagaaaat tatcccacac gctagagata gttggaatt      4260 tgtaacaaaa cttagacaac tagaaatgct ggaaaaccaa atctcaacta tacaccaatc      4320
atgccctagt caggaacacc aggaaattct attcaataat gtcagatggt tatccatcca      4380
gtctaagagg tttgcccctc tttacgcagt ggaagccaaa agaatacaga aactagagca      4440
taccattaac aactacatac agttcaagag caaacaccgt attgaaccag tatgtttgct      4500
agtacatggc agccccggaa caggtaaatc tgtagcaacc aacctgattg ctagagccat      4560
agctgaaaga gaaaacacgt ccacgtactc gctaccccg gatccatcac acttcgacgg      4620
atacaaacaa cagggagtgg tgattatgga cgacctgaat caaaacccag atggtgcgga      4680
catgaagctg ttctgtcaga tggtatcaac agtggagttt ataccaccca tggcatccct      4740
ggaggagaaa ggaatcctgt ttacttcaaa ttacgttcta gcatccacga actcaagcag      4800
aatttccccc cccactgtgg cacacagtga tgcattagcc aggcgctttg cgttcgacat      4860
ggacattcag gtcatgaatg agtattctag agatgggaaa ttgaacatgg ccatggctac      4920
```

-continued

```
tgaaatgtgt aagaactgtc accaaccagc aaactttaag agatgctgtc ctttagtgtg    4980
tggtaaggca attcaattaa tggacaaatc ttccagagtt agatacagta ttgaccagat    5040
cactacaatg attatcaatg agagaaacag aagatccaac attggcaatt gtatggaggc    5100
tttgttccaa ggaccactcc agtataaaga cttgaagatt gacatcaaga cgagtccccc    5160
tcctgaatgt atcaatgact tgctccaagc agttgactcc caggaggtga gagattactg    5220
tgagaagaag ggttggatag tcaacatcac cagccaggtt caaacagaaa ggaacatcaa    5280
cagggcaatg acaattctac aagcggtgac aaccttcgcc gcagtggctg gagttgtcta    5340
tgtcatgtat aaactgtttg ctggacacca gggagcatac actggtttac aaacaaaaa     5400 acccaacgtg cccaccatta ggacagcaaa ggtacaaggg ccaggttcg attacgcagt     5460 ggctatggct aaaagaaaca ttgttacagc aactactagc aagggagagt tcactatgtt    5520
aggagtccac gacaacgtgg ctattttacc aacccacgct tcacctggtg aaagcattgt    5580
gatcgatggc aaagaagtgg agatcttgga tgccaaagcg ctcgaagatc aagcaggaac    5640
caatcttgaa atcactataa tcactctaaa gagaaatgaa aagttcagag acattagacc    5700
acatatacct actcaaatca ctgagacaaa tgatggagtc ttgatcgtga acactagcaa    5760
gtaccccaat atgtatgttc ctgtcggtgc tgtgactgaa cagggatatc taaatctcgg    5820
tgggcgccaa actgctcgta ctctaatgta caactttcca accagagcag acagtgtgg    5880 tggagtcatc acatgtactg ggaaagtcat cgggatgcat gttggtggga acggttcaca    5940 cgggttttgca gcggccctga agcgatcata cttcactcag agtcaaggtg aaatccagtg    6000
gatgagacct tcgaaggaag tgggatatcc aatcataaat gccccgtcca aaccaagct    6060 tgaacccagt gctttccact atgtgtttga aggggtgaag gaaccagcag tcctcactaa    6120
aaacgatccc aggcttaaga caaactttga ggaggcaatt ttctccaagt acgtgggtaa    6180
caaaattact gaagtggatg agcacatgaa agaggcagta gaccactatg ctggccagct    6240
catgtcacta gacatcaaca cagaacaaat gtgcttggag gatgccatgt atggcactga    6300
tggtctagaa gcacttgatt tgtccaccag tgctggctac ccttatgtag caatgggaaa    6360
gaagaagaga gatatcttga acaaacaaac cagagacact aaggaaatgc aaaaactgct    6420
cgacacatat ggaatcaacc tcccactggt gacttatgta aaggatgaac ttagatccaa    6480
aacaaaggtt gagcagggga atccagatt aattgaagct tctagtttga atgactcagt    6540
ggcaatgaga atggcttttg gaacctata tgctgctttt cacaaaaacc caggagtgat    6600
aacaggttca gcagtagggt gcgatccaga tttgttttgg agcaaaattc cggtattgat    6660
ggaagagaag ctgtttgcct ttgactacac agggtatgat gcatctctca gccctgcttg    6720
gttcgaggca ctagagatgg tgcttgagaa aatcggattc ggagacagag ttgactacat    6780
cgactaccta aaccactcac accacctgta caagaataaa acatactgtg tcaagggcgg    6840
tatgccatct ggttgctcag gcacttcaat ttttaactca atgattaaca acttgattat    6900
caggacactc ttactgaaaa cctacaaggg catagattta gaccacctaa aaatgattgc    6960
ctatggtgat gatgtaattg cttcctaccc ccatgaagtt gacgctagtc tcctagccca    7020
atcaggaaaa gactatggac taactatgac tccagctgac aaatcagcta tatttgaaac    7080
agtcacatgg gagaatgtaa cattcttgaa gagattcttc agggcagacg agaaataccc    7140
atttcttatt catccagtaa tgccaatgaa ggaaattcat gaatcaatta gatggacaaa    7200
agatcctagg aacactcagg atcacgttcg ctctctgtgc ctattagctt ggcacaatgg    7260
cgaagaagaa tataacaaat tcctagctaa aatcaggagt gtgccaattg gaagagcttt    7320
```

```
attgctccca gagtactcaa cattgtaccg ccgttggctt gactcatttt agtaaccta    7380 cctcagtcga attggattgg gtcatactgc tgtaggggta aatttttctt taattcggag    7440
g                                                                    7441
```

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: Synthetic
      sequencing primer f or DNA amplification having multiple cloning
      site and 3C-protease cleavage site

<400> SEQUENCE: 2

```
gacaattgta tcataatgcc gcgggttaac cggccggctt tgttccaagg tgctcaggtt    60
tcttca                                                                66
```

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Peptide
      coded by SEQ. ID. NO. 2

<400> SEQUENCE: 3

Pro Arg Val Asn Arg Pro Ala Leu Phe Gln
1               5                   10

<210> SEQ ID NO 4
<211> LENGTH: 79
<212> TYPE: DNA
<213> ORGANISM: Artificial Sequence
<220> FEATURE:
<223> OTHER INFORMATION: Description of Artificial Sequence: primer for
      DNA amplification having multiple cloning site and 3C-protease
      cleavage site

<400> SEQUENCE: 4

```
attgtatcat aatgggtgct ccgcggggc cccggccggc tttgttccaa ggaggagcac     60
aggtttcatc acagaaagt                                                  79
```

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Peptide
      coded by SEQ. ID. NO. 4

<400> SEQUENCE: 5

Pro Arg Gly Pro Arg Pro Ala Leu Phe Gln Gly Gly Ala
1               5                   10

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence: Primer for
      DNA amplification having multiple cloning site and 3C-protease
      cleavage site

<400> SEQUENCE: 6

```
attgtatcat aatgggtgct ccgcggggc cccggccggc tttgttccaa ggagcacagg    60
tttcatcaca gaaagt                                                   76
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Primer for
      DNA amplification having multiple cloning site and 3C-protease
      cleavage site

<400> SEQUENCE: 7

```
atgggtgctc cgcgggttaa cctcgaggct ttgttccaag ga                      42
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Peptide
      coded by SEQ. ID. NO. 7

<400> SEQUENCE: 8

```
Pro Arg Val Asn Leu Gly Ala Leu Phe Gln Gly Ala
1               5                   10
```

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Primer for
      DNA amplification having multiple cloning site and 3C-protease
      cleavage site

<400> SEQUENCE: 9

```
gcgctagcac aggggcccgt taacctcgag aaggcacttg cgcaaggatt aggtcagatg    60
ctt                                                                  63
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Peptide
      coded by SEQ. ID. NO. 9

<400> SEQUENCE: 10

```
Gly Pro Val Asn Leu Gln Lys Ala Leu Ala Gln
1               5                   10
```

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: SstII-sense
      primer for DNA amplification having multiple cloning site and
      3C-protease cleavage site

<400> SEQUENCE: 11

```
aggcctccgc ggcctatagt gcagaacatc                                    30
```

<210> SEQ ID NO 12
<211> LENGTH: 30

```
<212> TYPE: DNA
<213> ORGANISM: Artificial Sequence
<220> FEATURE:
<223> OTHER INFORMATION: Description of Artificial Sequence:
      EagI-antisense primer for DNA amplification having multiple
      cloning site and 3C-protease cleavage site

<400> SEQUENCE: 12
aggcctcggc cgatagaacc ggtctacata                              30

<210> SEQ ID NO 13
<211> LENGTH: 18
<212> TYPE: DNA
<213> ORGANISM: Artificial Sequence
<220> FEATURE:
<223> OTHER INFORMATION: Desription of Artificial Sequence: cDNA
      synthesis primer

<400> SEQUENCE: 13
cgttgccgcc cccaccgt                                           18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: sense
      primer for DNA amplification covering nucleotide 680-697 of Sabin
      1 of poliovirus

<400> SEQUENCE: 14
cattgagtgt gtttactc                                           18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: antisense
      primer for DNA amplification covering nucleotide 797-814 of Sabin
      1 poliovirus

<400> SEQUENCE: 15
ggtagaacca ccatacgc                                           18

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: SstII-sense
      primer for DNA amplification

<400> SEQUENCE: 16
attaatccgc ggattaggcc agtagtatca                              30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      EagI-antisense primer for DNA amplification

<400> SEQUENCE: 17
attaatcggc cgactgtgcg ttacaatttc                              30
```

-continued

```
<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: sense primer for DNA amplification
<400> SEQUENCE: 18
aggcctccgc ggatgagcac aaatcctaaa 30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Antisense primer for DNA amplification
<400> SEQUENCE: 19
aggcctcggc cggggtagca ggagcca 27

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Sequence having multiple cloning site and 3C-protease cleavage site
<400> SEQUENCE: 20
ccgcgggtta accggccggc tttgttccaa 30

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: 3C Protease Cleavage Site
<220> FEATURE:
<221> NAME/KEY: misc_feature
<222> LOCATION: (2,3)
<223> OTHER INFORMATION: Xaa = Any Amino Acid

<400> SEQUENCE: 21

Ala Xaa Xaa Gln Gly
1 5

<210> SEQ ID NO 22
<211> LENGTH: 37
<212> TYPE: DNA
<213> ORGANISM: Human poliovirus 1

<400> SEQUENCE: 22
gtatcataat gggtgctcag gtttcatcac agaaagt 37

<210> SEQ ID NO 23
<211> LENGTH: 9
<212> TYPE: PRT
<213> ORGANISM: Human poliovirus 1

<400> SEQUENCE: 23

Met Gly Ala Gln Val Ser Ser Gln Lys
1 5

<210> SEQ ID NO 24

```
<211> LENGTH: 30
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 24
ccgcgggtta accggccggc tttgttccaa                                          30

<210> SEQ ID NO 25
<211> LENGTH: 30
<212> TYPE: DNA
<213> ORGANISM: Human poliovirus 1

<400> SEQUENCE: 25
gcgctagcac agggqttagg tcagatgctt                                          30

<210> SEQ ID N

```
-continued

<220> FEATURE:
<223> OTHER INFORMATION: Description of Artificial Sequence: 3C Protease
      Cleavage Site

<400> SEQUENCE: 30

Ala Leu Phe Gln
1
```